(12) United States Patent
Linderman et al.

(10) Patent No.: US 9,155,487 B2
(45) Date of Patent: Oct. 13, 2015

(54) METHOD AND APPARATUS FOR BIOMETRIC ANALYSIS USING EEG AND EMG SIGNALS

(76) Inventors: Michael Linderman, Ogdensburg, NY (US); Valery I. Rupasov, Gouverneur, NY (US)

( * ) Notice: Subject to any disclaimer, the term of this patent is extended or adjusted under 35 U.S.C. 154(b) by 901 days.

(21) Appl. No.: 13/341,465

(22) Filed: Dec. 30, 2011

(65) Prior Publication Data

US 2012/0172682 A1 Jul. 5, 2012

Related U.S. Application Data

(63) Continuation-in-part of application No. 12/588,675, filed on Oct. 23, 2009, now Pat. No. 8,280,503.

(60) Provisional application No. 61/108,603, filed on Oct. 27, 2008.

(51) Int. Cl.
*A61B 5/0488* (2006.01)
*A61B 5/0476* (2006.01)
*G06K 9/00* (2006.01)
*A61B 5/11* (2006.01)
*A61B 5/00* (2006.01)
*A61B 5/22* (2006.01)
*A61B 5/04* (2006.01)
*A61B 5/0492* (2006.01)

(52) U.S. Cl.
CPC ............ *A61B 5/0488* (2013.01); *A61B 5/0476* (2013.01); *A61B 5/4082* (2013.01); *A61B 5/6806* (2013.01); *A61B 5/7264* (2013.01); *G06K 9/00536* (2013.01); *A61B 5/04* (2013.01); *A61B 5/04012* (2013.01); *A61B 5/0492* (2013.01); *A61B 5/1101* (2013.01); *A61B 5/1125* (2013.01); *A61B 5/225* (2013.01); *A61B 5/4076* (2013.01); *A61B 5/4088* (2013.01); *A61B 5/4244* (2013.01); *A61B 5/7203* (2013.01); *A61B 5/7267* (2013.01); *A61B 5/7275* (2013.01); *A61B 5/7282* (2013.01)

(58) Field of Classification Search
CPC ...... A61B 5/04; A61B 5/0476; A61B 5/0488; A61B 5/04012; A61B 5/1101; A61B 5/1125; A61B 5/225; A61B 5/4076; A61B 5/4082; A61B 5/4088; A61B 5/7282; A61B 5/7275; A61B 5/7264
USPC .................................................. 600/544, 546
See application file for complete search history.

(56) References Cited

U.S. PATENT DOCUMENTS

| | | | |
|---|---|---|---|
| 8,190,249 B1 * | 5/2012 | Gharieb et al. | 600/544 |
| 2011/0130675 A1 * | 6/2011 | Bibian et al. | 600/544 |
| 2011/0306845 A1 * | 12/2011 | Osorio | 600/300 |

OTHER PUBLICATIONS

Berardelli et al., "Fast complex arm movements in Parkinson's disease", Journal of Neurology, Neurosurgery, and Psychiatry, vol. 49, 1986, pp. 1146-1149.*

* cited by examiner

*Primary Examiner* — Devin Henson

(57) ABSTRACT

Biometric assessment is performed by use of electromyography (EMG) signals detected from muscles at several locations on the hand/or other part of the body subject to fine motor control. In addition, electroencephalography (EEG), signals detect other biomarkers. The EMG and EEG signals are sensed, synchronized and registered. The signals are converted into digital data and are stored and processed for use in performing the biometric assessment.

3 Claims, 25 Drawing Sheets

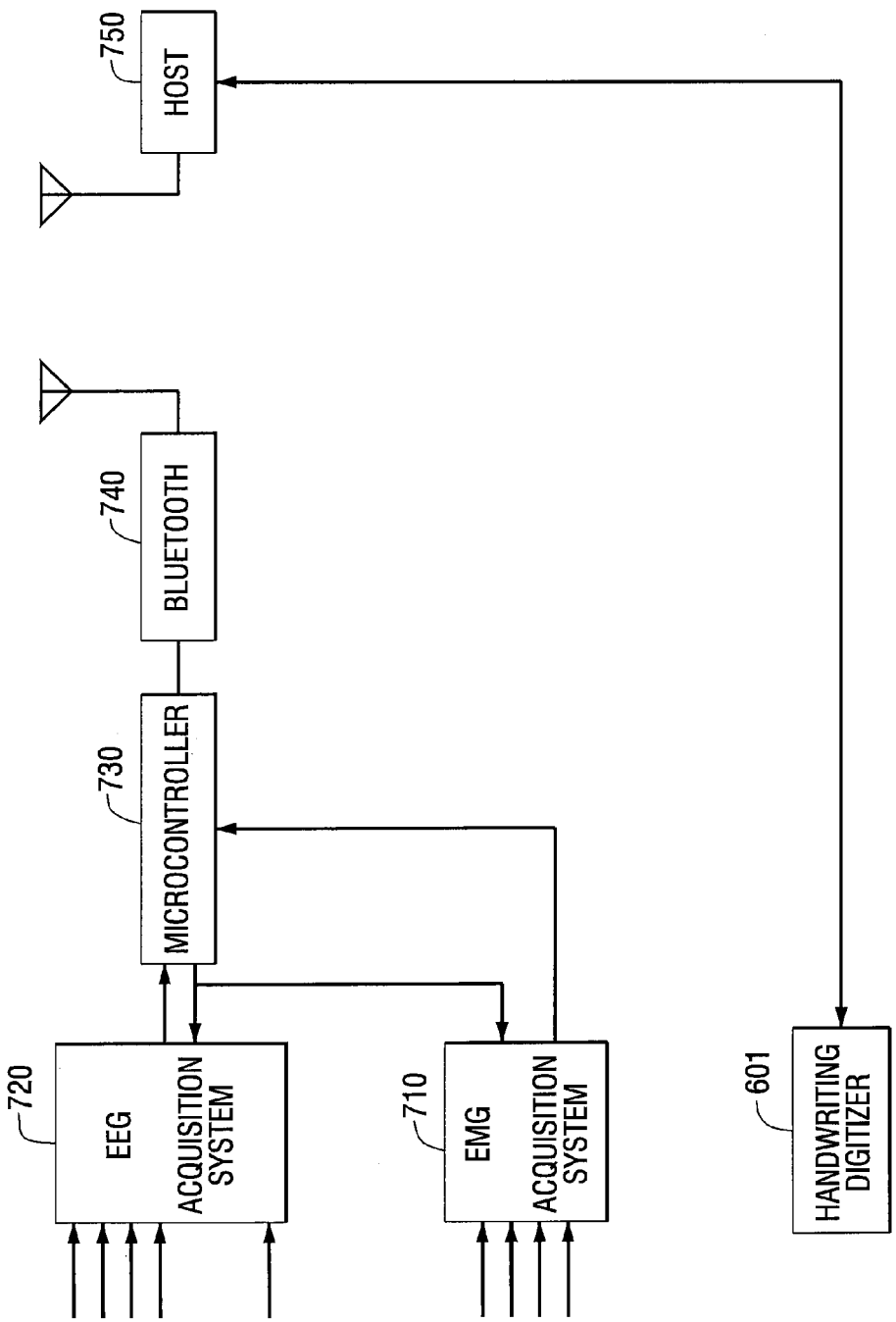

METHOD AND APPARATUS FOR BIOMETRIC ANALYSIS USING EEG AND EMG SIGNALS

CROSS-REFERENCE TO RELATED APPLICATION

This application is a continuation-in-part of U.S. patent application Ser. No. 12/588,675 filed Oct. 23, 2009, which claims the benefit of U.S. Provisional Application No. 61/108,603, filed Oct. 27, 2008, and U.S. patent application Ser. No. 11/640,954, filed Dec. 19, 2006, published as U.S. Published Application No. 2007-0140562, and which claims the benefit of U.S. Provisional Application No. 60/751,905, filed Dec. 21, 2005. The aforementioned provisional applications' disclosures are incorporated herein by reference in their entirety.

BACKGROUND

1. Field

This disclosure relates to the use of signals obtained from a limb (hand, and/or forearm, etc.) or other portion of the body subject to fine motor control, in medical diagnostics and biometrics, and to the use of electromyography (EMG) signals for medical, biometrics and related uses. The EMG is thereby used for the purposes of biometric assessment.

2. Background

The prior art is rich in various systems and methods in the area of digital handwriting, as well as various systems and methods relating to useful endeavors. In general, most existing systems and methods provide concrete functions, which have a defined response to a defined stimulus. Such systems, while embodying the "wisdom" of the designer, have a particular shortcoming in that their capabilities are limited.

According to the research that was conducted in Haifa University, handwriting problems are also clues to developmental, neurological, behavioral, or medical conditions such as ADHD and Parkinson's disease. Disturbances in handwriting legibility and speed (known as dysgraphia) are problematic for about 10-30% of elementary school-aged children. Many adults who suffer from neuromuscular pathologies of different types (e.g., Parkinson's disease, multiple sclerosis, Alzheimer's disease) also experience progressive deterioration of the quality of their handwriting. Dysgraphic writing has a variety of academic, emotional and social consequences. The comprehensive and detailed characterization of dysgraphia has diagnostic and treatment value, helping clinicians to differentiate between levels of motor involvement, to evaluate the effectiveness of medication and to achieve better techniques for handwriting remediation.

SUMMARY

Biometric assessment is performed by use of electrodes to sense electromyography (EMG) signals used for fine motor control by the subject. In one configuration, the signals are obtained from electrodes applied to the hand and/or forearm of a subject by use of a glove or similar garment. The sensed EMG signals are analyzed to detect patterns in the EMG signals.

The invention was based upon our discovery of biometric signals that can be analyzed to provide biomarkers for one or more disorders. The biometric signals can be collected and analyzed to provide four biomarkers, including two biomarkers from EMG signals and two from EEG signals. The biomarkers are based on identifying patterns of biometric signals in healthy subjects that are different from corresponding patterns in patients with disorders. For the particular disorder of Parkinson's Disease (PD), we found that (1) PD patients had EMG signals with evenly distributed intensities without distinctive short bursts, (2) PD patients had low correlations for the same channels, (3) PD patients demonstrated a growth of EEG correlations in cortex areas activated during handwriting, and (4) PD patients had EEG signals with correlations which endured over longer time intervals.

Using these discoveries we found, in general, that healthy subjects have one or more biometric signals which have defined patterns or characteristics during predetermined handwriting samples of one or more characters. However, patients with disorders such as PD have different biometric signals for the same handwriting samples. In other words, the patient with a disorder may be identified by having patterns of biometric signals with characteristics that do not correspond to the pattern of characteristics of the known healthy subjects. The results depend upon taking patient biometric signals over multiple, timed intervals of handwriting samples and time-stamping biometric signals during each interval of handwriting sample.

The invention may be embodied in one or more methods or one or more instruments or devices. Each embodied method or instrument or device may may detect one or more or all of the biomarkers that characterize a disorder. Each biomarker is, to some degree, a difference in between a pattern of biometric signals found in healthy subjects compared to a different pattern of biometric signals found in patients with PD or other disorders.

BRIEF DESCRIPTION OF THE DRAWINGS

The features, nature, and advantages of the present technique will become more apparent from the detailed description set forth below when taken in conjunction with the drawings in which like reference characters identify corresponding items throughout and wherein:

FIG. 7A is a high level schematic view of one embodiment of the invention.

DETAILED DESCRIPTION

Figure 1:
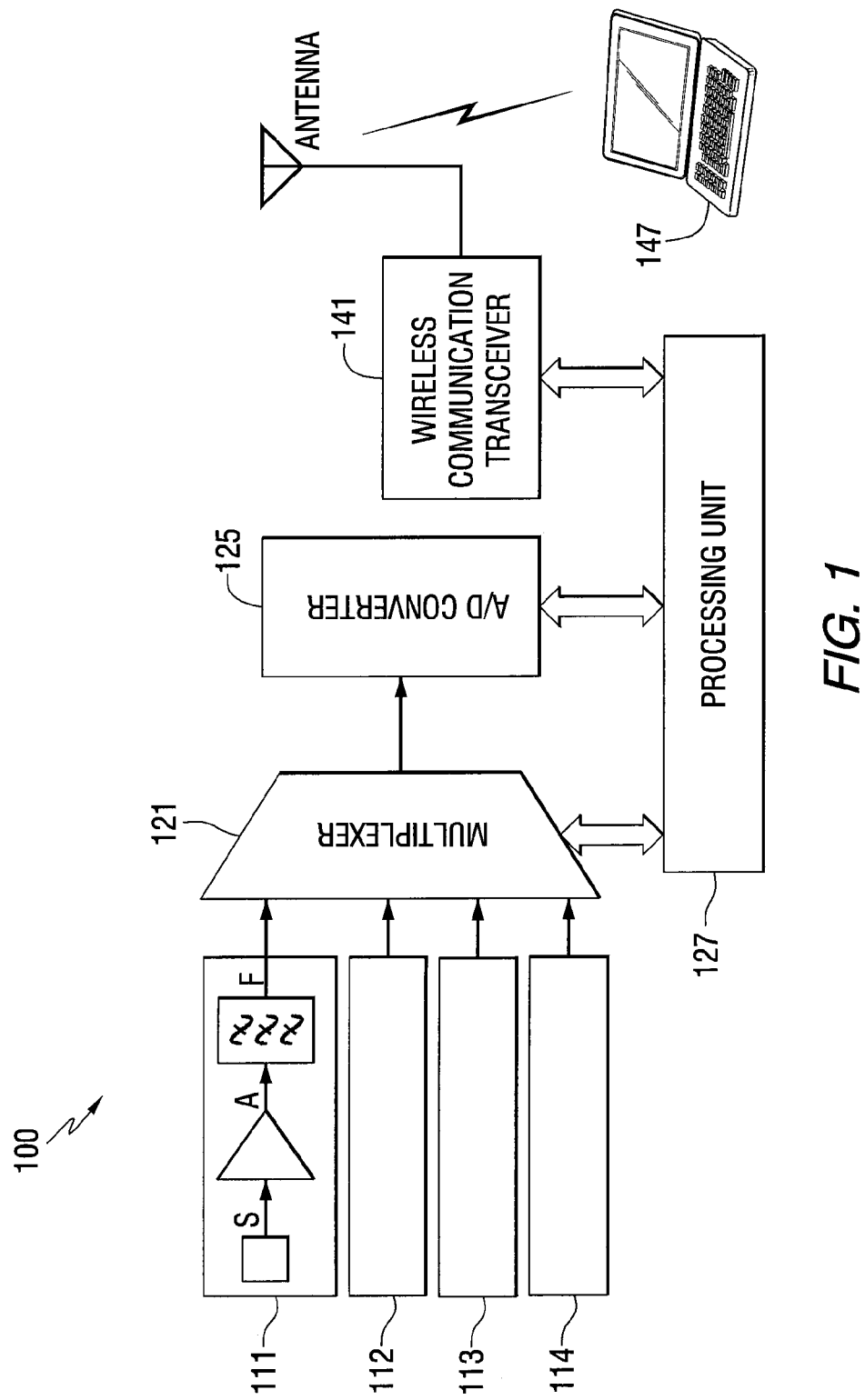
FIG. 1 is a schematic block diagram a circuit used to sense electromyographic (EMG) data and provide an output based on the sensed data.

The word "exemplary" is used herein to mean "serving as an example, instance, or illustration." Any embodiment described herein as "exemplary" is not necessarily to be construed as preferred or advantageous over other embodiments. The word "example" is used herein to mean "a non-limiting example." Each example provided herein is an illustration of merely one embodiment; many others may exist, and no provided example should be construed as limiting an otherwise broader category.

Overview

Handwriting activity is an example of fine motor control, and is characterized by sophisticated, controlled hand movement. Such hand motion activity resulting in controlled hand movement may be reconstructed in a digital format by applying computer algorithms directly to electromyography (EMG) signals. Pattern classification and recognition algorithms are used in conjunction with pattern recognition techniques. In the case of handwriting reconstruction, a recording is performed through a data processing routine, a handwriting reconstruction routine, and a routine that generates machine editable text.

Handwriting is given as an example of controlled hand movement; however other forms of fine motor control can be exhibited which are characteristic of sophisticated, controlled hand motion or sophisticated controlled fine motor control. In addition to fine motor control, fine motor control in combination with movement or holding of light or moderate weight (e.g., <5 kg) can be used to sense neurological conditions. Handwriting is a sophisticated form of controlled hand movement and is notable because it involves three factors:

memory;
knowledge; and
dexterity.

The last factor, dexterity, is the most familiar characteristic; however the other two factors are significant in handwriting activity and as such are also reflected in EMG patterns derived from sensing handwriting. Memory and knowledge are significant because a neurological or other biological process that affects the types of memory and knowledge used to perform handwriting activity would be detectable through the EMG patterns. This combination of memory, knowledge and dexterity is analogous to the "clock drawing test" used for testing for Alzheimer's dementia and other forms of dementia; however the combination of memory, knowledge and dexterity as expressed through handwriting is sensed as a part of controlled hand movement. Unlike the "clock drawing test", the combination of memory, knowledge and dexterity as expressed through handwriting can be sensed through EMG. Thus, the handwriting process represents a dynamic combination of conscious and subconscious activities.

A biosensor that can read the biometric signals from the muscles of a hand, and/or a forearm, using electromyography (EMG) is used to provide EMG signals. The EMG signals are then analyzed. The analysis can be used in medical diagnostics and biometrics, and in the use of EMG signals for medical, biometrics and related use, collectively referred to as biometric assessment.

While it is possible to use the EMG signals for handwriting recognition and, for the purposes of biometric assessment, the EMG signals are analyzed for features which can be related to either known patterns characteristic of a particular condition and/or for changes from one or more readings from the individual taken at different times. This software will process and interpret the biometric signals for the purposes of biometric assessment.

Effects of Biological Processes

One use for the biometric assessment is in the diagnosis of disease. By way of example, motor dysfunction is believed to have an association with liver cirrhosis and mild forms of hepatic encephalopathy. The mechanisms and clinical appearance of motor impairment in patients with liver cirrhosis are not completely understood; however, encephalopathy is a well known disease that develops as a result of liver malfunction. Encephalopathy refers to brain and nervous system damage that result from the liver's inability to metabolize toxins into harmless substances. More generally, in the case of liver disease, toxins build up in the body, causing various symptoms, one of which is difficulty with handwriting and other controlled hand movement. Fine motor control was studied in patients with advanced liver cirrhosis (excluding those with hepatic encephalopathy grade II) and 48 healthy controls using a kinematic analysis of standardized handwriting tests, and parameters of velocity, the ability to coordinate and the level of automatization of handwriting movements were analyzed. There is also believed to be an association between impairment of handwriting and other controlled hand movement with clinical neuro-psychiatric symptoms. It is expected that patients will show a statistically significant reduction of movement peak velocity in all controlled hand movement tasks as well as a substantial increase of number of velocity inversions per stroke. Using a z-score based assessment researchers have found impairments of handwriting in patients. The deterioration of handwriting was believed to be associated with clinical symptoms of motor dysfunction, such as bradykinesia, adi-adochokinesia, dysmetria of upper extremities and gait ataxia. This association suggests the application of kinematic analysis of handwriting for diagnostics of motor dysfunction in patients with mild forms of hepatic encephalopathy.

The analysis of EMG patterns, obtained from hand muscles during controlled hand movement can detect cognitive impairment and motor impairment much earlier than particular symptoms manifest themselves and will be noticed by people. The controlled hand movement can be, by way of non-limiting example, handwriting, such as writing alphanumeric characters, but can be other forms of handwriting and other forms of controlled hand movement. For the purposes of biometric assessment, it is not necessary to analyze handwriting per se, but rather the patterns of bio electricity, generated by neurons and muscles during some skilled hand movement.

EMG, as used for biometric assessment is useful in diagnostics of various medical diseases in a human body. The diagnostics can relate to deficiencies, injuries, malfunctions, and diseases, including but not limited to various forms of cancer, diabetes, genetic diseases, prenatal tests including but not limited to tests for Down syndrome, HIV, Parkinson's disease, Alzheimer's disease, multiple scleroses, brain injuries and stroke, hepatic disease, blood system disease and malfunctions, hormone system disease, nervous system diseases, central nervous system (CNS) diseases, autonomic nervous system changes and cerebral disorders. Many algorithms that are currently used to study EMG patterns in connection with hand and/or forearm movements can be also used to find associations with malfunctions of various organs. Liver cirrhosis, hepatic encephalopathy, and many others can affect various internal organs, like brain, lungs, blood, liver, spleen, stomach, etc. There are also publications about ongoing research identifying the associations between handwriting and heart diseases.

The disclosed use of EMG for biometric assessment can be use for diagnosis and monitoring of various types of heart diseases, which include: Coronary heart disease, cardiomyopathy, cardiovascular disease, ischaemic heart disease, heart failure, hypertensive heart disease, inflammatory heart disease, valvular heart disease. Also, other categories of heart diseases are possible to identify and monitor using the EMG for biometric assessment. Also, it is believed that the categories of diseases, as well as the diseases within categories of various organs (not just heart and heart related) and biological systems are potentially identifiable using the present disclosure.

In addition to medical diagnosis, the use of EMG for biometric assessment can be used to detect or analyze additional data related to an individual. This can be used in any convenient manner as desired by the subject, and can be used as a tool to analyze the person's biological or neurological state.

Basal ganglia dysfunction is believed to play a part in the pathophysiology of obsessive-compulsive disorder (OCD). The use of a computer aided technique for the analysis of hand movements allows the detection of subtle motor performance abnormalities, and can be applied in the study of patients with OCD and healthy controls. In one study, a digitizing graphic tablet was used to study hand motor performance in unmedicated patients with OCD and compared with healthy controls. All subjects drew superimposed concentric circles with both the right and the left hand, in addition to writing a given sentence, their personal signature, and letter sequences in four different sizes. Kinematic parameters were calculated to quantify hand motion. Subjects with OCD had significant impairments of handwriting performance, reflected by lower peak velocity and micrographia, as compared with controls and shortened acceleration phases per stroke. By contrast, in repetitive drawing, subjects with OCD had higher peak velocity than neurotypical control subjects. There were no significant differences in left and right hand performance between groups. Subjects with early versus late age of onset differed in handwriting parameters, such as handwriting consistency. Greater severity of obsessions and compulsions correlated with increasingly poor handwriting performance in subjects with OCD.

A subtle motor dysfunction in OCD can be detected with a digitizing tablet. The findings show handwriting impairments in patients with OCD, in line with the assumption that basal ganglia dysfunction is part of OCD pathophysiology. Repetitive motor pattern performance was not impaired, but rather tended to be even better in subjects with OCD than in controls. The findings also support the concept that subjects with OCD with early versus late age of onset differ in pathophysiological mechanisms and basal ganglia dysfunction.

Motor disturbances are a relevant aspect of depression. Kinematical analysis of movements can be applied to explore which type of motor dysfunction is associated with depression.

It is further believed that differences in sex hormones affect handwriting style. Digit ratio and sex role identity are believed to be influenced by prenatal hormone balances and can act as determinants of the sex as reflected in handwriting. Accordingly, there is a significant possibility of biological determinant of the judged gender of handwriting. It further found that there is a potential interplay between these variables and sex role identification. One biological marker that was identified was 2D:4D digit ratio (of index finger to ring finger length), which is negatively associated with prenatal testosterone and positively with prenatal oestrogen. In one example, handwriting samples were found to identify the gender of a statistically significant percentage of test groups. These ratings of handwriting gender correlated significantly with digit ratio. A more conservative analysis this time within each sex found that a women's right hand digit ratio correlated with relative sexuality of handwriting, but there was no corresponding relationship for the males. These findings suggest that prenatal hormonal influences can affect later female handwriting performance and might even affect developmental inter-hemispheric differences, but do not appear to impact on males.

EMG principal component analysis of finger spelling has been used to demonstrate that within a single hand shape transmission, different muscles become active at different times and for somewhat different durations. Thus, muscle activation waveforms are asynchronous and can not be adequately described in terms of a single command wave form acting as a common drive to groups of agonists and antagonists. On the other hand, the average EMG levels revealed instances of co-activation and reciprocal activation of muscle pairs. This can suggest that hand movements may be generated by activity waves unfolding in time.

For pattern identification it is important to analyze the EMG activity from various muscles. This is because the EMG recordings taken during movements of different fingers indicate that a given muscle could act as an agonist, antagonist, or stabilizer of the digits it serves. Furthermore, during a given finger movement, several different muscles typically were active. Therefore, their results indicated that individuated finger movements were produced not by independent sets of muscles acting on each digit, but by the activity of several muscles, many of which act on more than one digit, combined such that the net effect was movement of one digit more than others.

Patient Monitoring

EMG has the advantage that it makes it possible to measure changes in the individual person. In addition, it is possible for an individual with a medical condition to self-monitor either the condition or the effects of treatments. By way of example, the individual can use EMG biometric assessment to monitor the effects of a drug used by that individual.

In particular, certain drugs have effects on a patient's physical activity, some of which are very visible. For example, it is possible to identify caffeine withdrawal by a slight shaking, for example while lifting a lightweight object. A person using some benzodiazapine drugs would have a particular type of jerky hand movement.

It is often difficult for a physician to objectively evaluate a patient's pain or other internal reactions because in many cases, the physician must rely on subjective data either from the patient or from direct observation. EMG could be used to evaluate the reaction, because the effect of a particular condition on hand movement as detected by EMG is substantially less subjective. In this manner, the physician would have the ability to use a standardized test, measured by EMG, with the results being analyzed by the EMG.

Another issue would be that if it is possible to measure an effect of a condition, it is also possible to very quickly analyze a treatment or supposed "cure". This becomes particularly true in cases where the condition is identified by a marker and the treatment has an effect that extends beyond the effects of that treatment that can be expected absent the condition being treated. Thus, EMG recorded during target standardized repeatable movements can be used in a clinical setting as a measurement parameter to determine a disease and its severity that may be done by applying various algorithms. The methods of statistical analysis, neural networks, and other pattern recognition techniques may be useful in medical diagnosis through EMG.

Accordingly, EMG signals can be examined for patterns which are characteristic of particular illnesses and conditions. In this sense, the disease or condition will reveal itself on EMG signals that are recorded during standard handwriting, controlled hand movement or another target movement, regardless of whether the indications are an apparent part of the subject's "handwriting" or handwriting as reflected by EMG patterns. In this sense, the patterns are different from patterns used for detection of handwriting patterns per se. Therefore, the handwriting or other controlled hand movement as reflected by EMG functions as a "carrier" for signals used for diagnosis.

The same device can supply the data over time to a larger knowledge base computerized system containing all medical and biological information about a human body, its organs, and systems that was received from the analysis of EMG during controlled hand movement activity. A database of a single person can accept the data from other databases, including of one's parents for various searches, including identifying "controlled hand movement EMG" patterns of genetic diseases. Databases of various organs and systems and larger knowledge bases can be scanned from time to time and appropriate warnings can be given to a person. This historical data about the body activity and bio status can be located locally or remotely. The output from this medical device can go to other analytical databases.

This disclosure relates to the diagnostics of various malfunctions or diseases of all body organs and interconnecting biological systems in a body. Various examples of organs, injuries, and diseases are provided just to illustrate the wide range of applications that this disclosure can be used for. The techniques can be also applied to characterize healthy people.

Observing Learned Behavior

The subject can be observed during learning in order to measure the subject's response during the learning process. This provides a means to assess the learning process in the subject, based on quantitative measurements obtained by EMG. These measurements can then be used to determine the learned response. The learned response can be directly transferred to controlled hand movement, as in learning an alphabet or pattern such as characters in the PalmPilot™ Grafiti™ alphabet, learning to draw or replicate a pattern, or as a measured secondary response sensed through controlled hand movements during a diverse learning process. The EMG is measured or recorded during standardized learning procedures to provide a quantifiable assessment of the subject's learning process.

Nerve Sensing

All organs and biological systems are regulated through the nervous system. The brain is the center of the nervous system. The human brain contains roughly 100 billion neurons, each linked with up to 10,000 synaptic connections. These neurons communicate with one another by means of long protoplasmic fibers called axons, which carry trains of signal pulses called action potentials to distant parts of the brain or body and target them to specific recipient cells. In one sense, it might be said that the most important function of the brain is to serve as the physical structure underlying the mind. From a biological point of view, though, the most important function is to generate behaviors that promote the welfare of an animal. The brain controls behavior either by activating muscles, or by causing secretion of chemicals such as hormones. In case of malfunction of a biological system, or internal organs, the nervous system is going to change its behavior.

Controlled hand movement is controlled by the motor system. Motor systems are areas of the brain that are more or less directly involved in producing body movements, that is, in activating muscles. With the exception of the muscles that control the eye, all of the voluntary muscles in the body are directly innervated by motor neurons in the spinal cord, which therefore is the final common path for the movement-generating system. Spinal motor neurons are controlled both by neural circuits intrinsic to the spinal cord, and by inputs that descend from the brain. The intrinsic spinal circuits implement many reflex responses, and also contain pattern generators for rhythmic movements such as walking or swimming. The descending connections from the brain allow for more sophisticated control.

The brain contains a number of areas that project directly to the spinal cord. At the lowest level are motor areas in the medulla and pons. At a higher level are areas in the midbrain, such as the red nucleus, which is responsible for coordinating movements of the arms and legs. At a higher level yet is the primary motor cortex, a strip of tissue located at the posterior edge of the frontal lobe. The primary motor cortex sends projections to the subcortical motor areas, but also sends a massive projection directly to the spinal cord, via the so-called pyramidal tract. This direct corticospinal projection allows for precise voluntary control of the fine details of movements.

Other "secondary" motor-related brain areas do not project directly to the spinal cord, but instead act on the cortical or subcortical primary motor areas. Among the most important secondary areas are the premotor cortex, basal ganglia, and cerebellum.

The premotor cortex (which is actually a large complex of areas) adjoins the primary motor cortex, and projects to it. Whereas elements of the primary motor cortex map to specific body areas, elements of the premotor cortex are often involved in coordinated movements of multiple body parts.

The basal ganglia are a set of structures in the base of the forebrain that project to many other motor-related areas. Their function has been difficult to understand, but one of the most popular theories currently is that they play a key role in action selection. Most of the time they restrain actions by sending constant inhibitory signals to action-generating systems, but in the right circumstances, they release this inhibition and therefore allow their targets to take control of behavior.

The cerebellum is a very distinctive structure attached to the back of the brain. It does not control or originate behaviors, but instead generates corrective signals to make movements more precise. People with cerebellar damage are not paralyzed in any way, but their body movements become erratic and uncoordinated.

In addition to all of the above, the brain and spinal cord contain extensive circuitry to control the autonomic nervous system, which works by secreting hormones and by modulating the "smooth" muscles of the gut. The autonomic nervous system affects heart rate, digestion, respiration rate, salivation, perspiration, urination, and sexual arousal—but most of its functions are not under direct voluntary control.

One example of a biological system associated with the nervous system would be the lungs and central nervous system (CNS), because CO2 levels in the blood change blood PH, which is sensed as being out of breath. Further breathing itself is controlled by the CNS. This will affect the EMG signals during controlled hand movement activity. Similarly, many digestive functions interact with the CNS. As a practical matter, this relates to the entire body, since general health and things such as exhaustion are known to affect hand movement.

Due to the clinical nature of EMG, the same signals obtained during controlled hand movement may provide a quantifiable way of clinical diagnostics. For the most accurate interpretation, EMG signals have to go through the processes of noise reduction, filtration, rectification, integration, amplification, differentiation, and/or other necessary modifications. All these processes can be described as algorithms. In addition, other processing algorithms should be employed in order to identify repetitive activities, such as patterns of EMG digital representations. Thus, one would employ preparation, recognition, and classification, and/or other algorithms to identify patterns derived from the electrical signals, obtained from muscles of hands and/or forearms, etc., via surface sensing electrodes and during the controlled hand movement activity of an individual. These patterns of signals should be associated with a particular disease/malfunction, or plurality of diseases, or malfunctions, when a particular organ or the plurality of organs, do not function in the normal way for an individual with particular age and internal, or external conditions.

One of the useful endeavors of controlled hand movement that people were trying to explore over a long period of time is to understand the individual characteristics of a person, including their clinical conditions. Almost every book written on handwriting analysis incorporates at least a paragraph, and often chapters, on clinical graphology; however, very few scientific papers seem to have been published by the authors to validate the claims. Alternatively, this disclosure is based on the fact that the nature of EMG during handwriting or other controlled hand movement is fundamentally different from the nature of mechanical recording of handwriting or similar repeatable movement. EMG is directly related to the activity of the neurons that are located in a spinal cord. The handwriting process represents a dynamic combination of conscious and subconscious activities. Therefore, in this disclosure EMG is not merely a media that can be used to calculate mechanical movements, but rather it is a measurable parameter representing a combined state of a clinical condition. In this context, EMG that is recorded during handwriting, controlled hand movement or another target movement can be used as an accurate indicator of an appearance, or a change in a disease, as well as a predisposition to a disease. Finally, since the behaviors of people in some respect is determined by the conditions and developments of their organs and biological systems supporting those organs, this disclosure can be used for understanding and evaluating the behaviors and character traits of healthy subjects and finding their predispositions, and compatibilities. The examples include, but not limited to the information about personality, pregnancy, sex of the baby, etc.

In a broad conceptually, the EMB biometric assessment apparatus comprises two components; a biosensor and a pattern recognition module. The biosensor includes physical sensors on a garment, such as a glove or a glove with a forearm extension. The sensors are able to read the biometric signals from the body, using electromyography (EMG). In the case of a glove, the signals are read from nerve connections to the muscles of a hand, and/or a forearm, using EMG.

The EMG signals are provided to the pattern recognition modules. The pattern recognition module includes pattern recognition and extraction software. This software will process and interpret the biometric signals for the purposes of identifying of a malfunction or a disease of organ, or the plurality of organs in a human body. The same device can be extended to process and interpret additional data related to an individual at the time when controlled hand movement takes place. Biometric assessment therefore is implemented with a device, a method, and a system for digital recordation, storage, displaying, and communication system that may be extended to processing of additional related information, such as the medical condition of the human body. This instantaneous controlled hand movement EMG recording system may be combined with other forms of communication and data processing, and control such as phones (e.g. SMS/MMS messages), medical devices, translators, telerobotics, games, sports, etc.

Sensing of EMG

This process incorporates a method, device and system for reading, interpreting, and processing the EMG related data, obtained during handwriting activity, drawing and/or other controlled hand movement. This technique is based on biometric signals. While handwriting analysis is discussed, in cases in which EMG is used for biometric assessment, the actual analysis of the written material or the handwriting for purposes other than for biometric assessment may be superfluous because in the case of biometric assessment, the handwriting is a tool. Nevertheless, there may be cases in which the information obtained from biometric assessment may be used to augment the analysis of handwriting, for example as an assistive tool for a person with ataxia or for facilitated communication.

It is believed that biometric signals from muscles and other neural communications contain the most complete data pertaining to the controlled hand movement activity. This data is used for interpretation with programming algorithm. The purpose of this controlled hand movement recordation device is to accurately interpret the medical conditions of various organs in a human body. This recorded data may also be processed to translate the information into human readable format in the same device or elsewhere.

The system also includes the pattern recognition algorithm that will interpret the biometric signals. Another programming algorithm will process and translate the information. The program will be capable of displaying a message for a patient and/or a medical professional in a readable format for itself or passing it to a viewer or word processor. The program can also process the received information in any convenient manner. The user should be able to input some additional information for a device to take into account and use in conjunction with the data obtained from EMG.

Configuration

In one general aspect, the disclosure incorporates an approach to record controlled hand movement activity, based on a biosensor that is reading the biometric signals from the muscles and/or neural communications. These biosensors may be located on a surface of a hand including fingers and/or a forearm. The biosensor based device is independent of an actual writing instrument, and the user can use any writing instrument or a finger to write on any paper or just on a plain surface. The data processing unit and a memory chip for a biosensor maybe also located in an abbreviated glove, a watch, wristband, a sleeve, or some other article of apparel. The biosensor may also collect other biometric signals, voice, or textual data to be interpreted and combined with a cell phone, and/or other devices. The device may be independent from another electronic device that will be used to display the interpretation of biometric signals, in which case, the data can be transmitted to another device at the same time, or at a later time. Prior to transmission, the data may be stored and/or immediately transmitted to another electronic device, if needed. In addition, it is possible to incorporate some basic and/or more sophisticated displaying capabilities on a recording or storage device used for temporary storage of the biometric data.

This described technique uses the fact that EMG signals can be used to digitize controlled hand movement and effectively creating the device to transfer the controlled hand movement activity into a computer device. This technology allows for a mini glove to record EMG while the users write or draw, using fingers, any writing instrument. This recorded information may be stored locally in a memory chip and then transferred to a computer, or a cell phone.

The technique is implemented with pattern recognition algorithms that provide the correlation between the medical status of human organism and EMG signals. In addition, it takes advantage of dry electrodes applied to skin locations through a mini glove. This disclosure will be used in consumer electronics, education, medicine, telerobotics, sports, and many other fields, since EMG can be interpreted in various domains, like time, frequency, and dimensions.

The data apparel for instantaneous EMG recording during controlled hand movement uses three design principles:
 Dry EMG electrodes
 EMG data acquisition system
 Pattern recognition algorithms While dry EMG electrodes provide advantages in terms of convenience of use, it is also possible to use electrodes requiring gel connections or other types of wet electrodes.

These design principles can be used in a biomedical application, where EMG is a measurable parameter of a particular biomedical condition, such as heart failure. In that case, EMG electrodes can be applied by a professional and may or may not include a glove; however, a glove, special sleeve, or similar article of apparel still can be also used for preliminary tests.

Controlled hand movement activity that is represented by EMG signals is captured in a digital format by applying computer algorithms to processed (filtered, pretreated and digitized) electromyography (EMG) signals. Pattern classification and recognition algorithms are used in conjunction with pattern recognition techniques. The recording is done through a data processing apparatus and routine, handwriting, controlled hand movement or another target movement interpretation routine, and a routine that generates an output.

Applying computer algorithms to EMG signals that are recorded during handwriting, controlled hand movement or another target movement may help in diagnosis of various diseases, and monitoring a rehabilitation or recovery process. Finally, since the behaviors of people in some respect is determined by the conditions and developments of their organs and biological systems supporting those organs, this disclosure can be used for understanding and evaluating the behaviors and character traits of healthy subjects and finding their characteristics, predispositions, and compatibilities.

Mathematical Filtering Techniques

EMG and hand gesture recognition can be performed by collecting surface EMG signals using dry electrodes. In theory, muscle activity originating from different muscles can be considered independent and this gives an argument to the use of Independent Component Analysis (ICA) for separation of muscle activity originating from the different muscles. The outcome of ICA is that the signals are separated without there being any information of the order of the sources. In addition to ICA the activities of different muscles are classified using back-propagation neural networks. Dry electrodes that are used to sense the EMG data from the surface of the body have to be very sensitive, low maintenance, and should not require any skin preparation.

The data acquisition system has to be computation and energy efficient with a very small footprint. In a normal use it is enough to have surface electrodes inside of the appropriate apparel. Sometimes, internal electrodes will be required.

In the past, when EMG was used to identify movement, the systems were limited as suitable for only gross actions, and when there was one prime-mover muscle involved. The present technique uses signal processing and mathematical models and thereby makes it practical to implement advanced EMG detection and analysis techniques. Various mathematical techniques and Artificial Intelligence (AI) have received extensive attraction. Mathematical models include wavelet transform, time-frequency approaches, Fourier transform, Wigner-Ville Distribution (WVD), statistical measures, and higher-order statistics. AI approaches towards signal recognition include Artificial Neural Networks (ANN), Dynamic Recurrent Neural Networks (DRNN), and fuzzy logic systems.

A variety of mathematical filtering techniques can be used to enhance EMG analysis. The accuracy of hand gesture recognition using surface EMG includes statistical analysis and neural networks for applications in prosthetic devices, to provide an intelligent and simple system to recognize fairly complex hand movements and provide a user assessment routine to evaluate the correctness of executed movements. This can be implemented using an Adaptive Neuron-Fuzzy Inference System (ANFIS) integrated with a real time learning scheme to identify hand motion commands. The ANFIS method can be utilized as part of a hybrid method for training the fuzzy system, comprising Back Propagation (BP) and Least Mean Square (LMS). A subtractive clustering algorithm can then be used in order to optimize the number of fuzzy rules. In order to design a pattern recognition system Time Domain (TD) and time Frequency Representation (TFR) may be used, and in order to decrease the undesirable effects of the dimension of these feature sets, Principle Component Analysis (PCA) may be utilized.

Monte-Carlo tree search can be used in combination with EMG data for diagnostics of various diseases and organs malfunctions. Also, these are just the examples of the algorithms that can be used to identify medical patterns. Variations and combinations of these and additional algorithms can be used as well. Linear Discriminant Analysis, Bayesian methods, hidden Markov chains, Fourier analysis, Fast Fourier Transform (FFT), adaptive neuro-fuzzy inference system, adaptive signal processing, back propagation, least mean square, Artificial Neural Network (ANN), autoregressive, mean absolute value, slope sign changes, zero crossing, principal component analysis, common mode rejection ratio, membership function, time domain (features), time frequency representations, fuzzy interference system, discrete wavelet transform, root mean square.

Pattern Recognition Algorithms

A raw sensed output of EMG signals does not make any sense as interpretations of hand movement. It is only when one applies EMG interpretation algorithms to the raw sensed output that one is able to interpret the signals as a meaningful activity and find the correspondence with the fine grained hand movements. This is because there is no direct correspondence between sensed EMG of muscles and fine grained hand movements associated with the sensed EMG. Additionally, all muscles generate EMG signals, irrespective of whether the fingers are moving or not.

Pattern recognition aims to classify data (patterns) based on either an a priori knowledge or on statistical information extracted from the patterns. The patterns to be classified are usually groups of measurements or observations represented as data points in an appropriate multidimensional space.

A complete pattern recognition system includes a sensor that gathers the observations to be classified or described; a feature extraction algorithm that computes numeric or symbolic information from the observations; and a classification or description scheme that does the actual job of classifying or describing observations, relying on the extracted features.

The classification or description scheme is usually based on the availability of a set of patterns that have already been classified or described. This set of patterns is termed the training set and the resulting learning strategy is characterized as supervised learning. Learning can also be unsupervised, in the sense that the system is not given an a priori labeling of patterns, instead it establishes the classes itself based on the statistical regularities of the patterns.

The classification or description scheme usually uses one of the following approaches: statistical (or decision theoretic), or syntactic (or structural). Statistical pattern recognition is based on statistical characterizations of patterns, assuming that the patterns are generated by a probabilistic system. Structural pattern recognition is based on the structural interrelationships of features. A wide range of algorithms can be applied for pattern recognition, from very simple Bayesian classifiers to much more powerful neural networks. Further information is found in, Sergios Theodoridis, Konstantinos Koutroumbas, Pattern Recognition (3rd edition, 2006)

Multiple Linear Regression

In statistics, multiple linear regression is a regression method of modeling and predicting the conditional expected value alone variable y given the values of some other variable or variables x. Linear regression is called "linear" because the relation of the response to the explanatory variables is assumed to be a linear function of some parameters. It is often erroneously thought that the reason the technique is called "linear regression" is that the graph of $y=\alpha+\beta x$ is a line. In contrast, if the model is, by way of example:

$$y_i = \alpha + \beta x_i + \gamma x_i^2 + \epsilon_i$$

(in which case the vector $(x_i, x_i^2)$ is placed the role formerly played by $x_i$ and the vector $(\beta, \gamma)$ is placed in the role formerly played by $\beta$), then the problem is still one of linear regression, even though the graph is not a straight line.

Regression models which are not a linear function of the parameters are called nonlinear regression models (for example, a multi-layer artificial neural network).

More generally, regression may be viewed as a special case of density estimation. The joint distribution of the response and explanatory variables can be constructed from the conditional distribution of the response variable and the marginal distribution of the explanatory variables. In some problems, it is convenient to work in the other direction: from the joint distribution, the conditional distribution of the response variable can be derived. Regression lines can be extrapolated, where the line is extended to fit the model for values of the explanatory variables outside their original range.

Bayesian Classifier

Another pattern recognition model is called Bayesian classifier. This is a probabilistic classifier based on applying Bayes' theorem with strong independence assumptions. In spite of their naive design and apparently over-simplified assumptions, naive Bayesian classifiers often work much better in many complex real-world situations than might be expected. Recently, careful analysis of the Bayesian classification problem has shown that there are sound theoretical reasons for the seemingly unreasonable efficacy of naive Bayesian classifiers, Abstractly, the probability model for a classifier is a conditional model:

$$p(C|F_1, \ldots, F_n)$$

over a dependent class variable C with a small number of outcomes or classes, conditional on several feature variables $F_1$ through $F_n$. The problem is that if the number of features, n, is large or when a feature can take on a large number of values, then basing such a model on probability tables is infeasible and computationally demanding. The model is therefore reformulated to make it more tractable.

Using Bayes' theorem, we write $$p(C \mid F_1, \ldots, F_n) = \frac{p(C)p(F_1, \ldots, F_n \mid C)}{p(F_1, \ldots, F_n)}.$$

In practice only the numerator of that fraction is of interest, since the denominator does not depend on C and the values of the features $F_1$ are given, so that the denominator is effectively constant. The numerator is equivalent to the joint probability model $$p(C, F_1, \ldots, F_n)$$

which can be rewritten as follows, using repeated applications of the definition of conditional probability:

$$p(C, F_1, \ldots, F_n) = p(C)p(F_1, \ldots, F_n \mid C)$$

$$= p(C)p(F_1 \mid C)p(F_2, \ldots, F_n \mid C, F_1)$$

$$= p(C)p(F_1 C)p(F_2 \mid C, F_1)$$

$$p(F_3, \ldots, F_n \mid C, F_1, F_2)$$

$$= p(C)p(F_1 \mid C)p(F_2 \mid C, F_1)p(F_3 \mid C, F_1, F_2)$$

$$p(F_4, \ldots, F_n \mid C, F_1, F_2, F_3)$$

and so forth. Now the "naive" conditional independence assumptions come into play: assume that each feature $F_i$ is conditionally independent of every other feature $F_j$ for $j \neq i$. Therefore:

$$p(F_i|C,F_j)=p(F_i|C)$$

and so the joint model can be expressed as:

$$p(C, F_1, \ldots, F_n) = p(C)p(F_1 | C)p(F_2 | C)p(F_3 | C) \ldots$$

$$= p(C)\prod_{i=1}^{n} p(F_i | C).$$

Under the above independence assumptions, the conditional distribution over the class variable C can be expressed according to:

$$p(C | F_1, \ldots, F_n) = \frac{1}{Z}p(C)\prod_{i=1}^{n} p(F_i | C)$$

where Z is a scaling factor dependent only on $F_1, \ldots, F_n$, i.e., a constant if the values of the feature variables are known.

Models of this form are much more manageable, since they factor into a so-called class prior p(C) and independent probability distributions $p(F_i|C)$. If there are k classes and if a model for $p(F_i)$ can be expressed in terms of r parameters, then the corresponding naive Bayes model has (k−1)+n r k parameters. In practice, often k=2 (binary classification) and r=1 (Bernoulli variables as features) are common, and so the total number of parameters of the naive Bayes model is 2n+1, where n is the number of binary features used for prediction. Further information is found in, Domingos, Pedro & Michael Pazzani, "On the optimality of the simple Bayesian classifier under zero-one loss". *Machine Learning*, 29:103-137, (1997).

Despite the fact that the far-reaching independence assumptions are often inaccurate, the naive Bayesian classifier has several properties that make it very useful in practical applications. In particular, the decoupling of the class conditional feature distributions means that each distribution can be independently estimated as a one dimensional distribution. This in turn helps to alleviate problems stemming from the curse of dimensionality, such as the data sets that scale exponentially with the number of features. Like all probabilistic classifiers under the MAP decision rule, it arrives at the correct classification as long as the correct class is more probable than any other class; hence class probabilities do not have to be estimated very well. Thus, the overall classifier is robust enough to cope with the deficiencies in its underlying naive probability model. Further information is found in, Hand, D J, & Yu, K. "Idiot's Bayes—not so stupid after all?" International Statistical Review, Vol 69 part 3, (2001), pages 385-399.

Artificial Neural Network

An artificial neural network (ANN), such as Time Lagged Recurrent Network (TLRN) or commonly just neural network (NN) is an interconnected group of artificial neurons that uses a mathematical model or computational model for information processing based on a connectionist approach to computation. In most cases an ANN is an adaptive system that changes its structure based on external or internal information that flows through the network. (The term "neural network" can also mean biological-type systems.)

In more practical terms neural networks are non-linear statistical data modeling tools. They can be used to model complex relationships between inputs and outputs or to find patterns in data.

There is considerable overlap between the fields of neural networks and statistics. Statistics is concerned with data analysis. In neural network terminology, statistical inference means learning to generalize from noisy data. Some neural networks are not concerned with data analysis (e.g., those intended to model biological systems) and therefore have little to do with statistics. Some neural networks do not learn (e.g., Hopfield nets) and therefore have little to do with statistics. Some neural networks can learn successfully only from noise-free data (e.g., ART or the perception rule) and therefore would not be considered statistical methods. Most neural networks that can learn to generalize effectively from noisy data have at least some similarity in technique with statistical methods.

Hardware Implementation

FIG. 1 is a diagram illustrating exemplary circuit 100 used to sense electromyographic (EMG) data and provide an output based on the sensed data. The circuit 100 detects biometric signals obtained from sensing stimulation of muscles. It can be seen that these signals are distinct and not chaotic. There is a correlation between the muscle activities and movements of fingers, hand, and arm via programming algorithms, e.g., pattern recognition. The special pattern recognition algorithms are required, because the correlation is not direct. The controlled hand movement recordation device contains the biosensor that may be in a form of MEMS system as it should be very small. A biosensor also can be an electrode for recording Electromyography (EMG) signals. This sensor may have an amplifier to increase the signal to noise ratio. The device will have a way to store the data after it is read and/or to transmit the data to where it will be processed for interpretation and/or displayed. Intermediate systems may also be included for other purposes.

Figure 2:
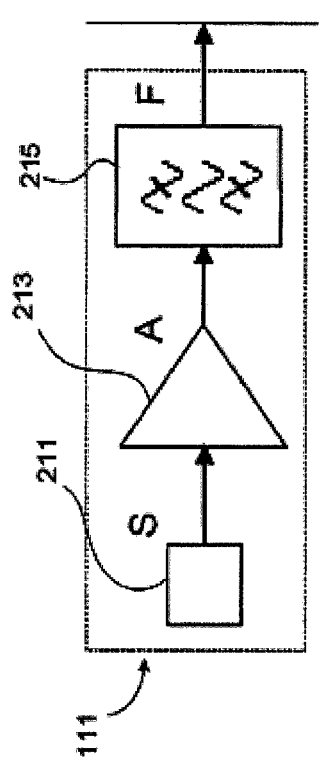
FIG. 2 is a diagram showing details of one of the sensor circuits of FIG. 1.

Depicted in FIG. 1 is a plurality of sensor circuits 111, 112, 113, 114, a multiplexer 121, an analog-to-digital converter 125, and a processing unit 127. Also depicted is a wireless communication transceiver 141 which can communicate with an external computer 147. FIG. 2 is a diagram showing details of one of the sensor circuits 111 depicted in FIG. 1. The sensor unit includes a sensor electrode 211, an amplifier 213 and an output filter 215.

Figure 3:
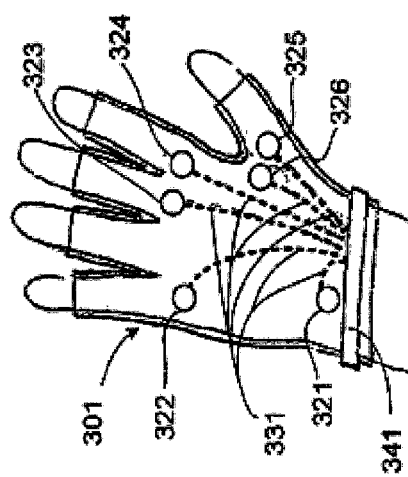
FIG. 3 is a diagram showing an example of a user interface garment.

FIG. 3 is a diagram showing an example of a user interface garment 301. The garment can be in the form of a lightweight glove or "mini glove", such as the "fingerless glove" depicted. The glove has attached thereto a set of sensing electrodes 321, 322, 323, 324, 325, 326 and a corresponding set of electrical connections 331. The electrical connections are connected to a processing module 341, which includes the circuitry depicted in FIG. 1.

It is understood that the specific structure of the glove is not part of the disclosure. It is also possible to provide any convenient form of attachment for the electrodes, not limited to a glove-like structure. It is further possible to mount one or more of the sensing electrodes 321-326 to parts of the body separate from the hand (e.g., on the arm), and it is possible to mount one or more of the sensing electrodes 321-326 separate from the glove. The use of five electrodes is presented as an example, for clarity of the drawings and does not represent the expectations of actual construction.

It is anticipated that the actual locations of the electrodes will differ from that shown in the diagram, as the locations are selected for optimal sensing. Examples of locations which may be selected include area between the thumb and first finger on the palm side, on the back of the hand between the thumb and first finger, on the back of the hand, on the bony part in alignment with the fourth finger, and on the wrist on front and back sides of the hand these locations are given by way of example, as the actual locations are in accordance with optimal EMS sensing.

The components of the sensors can be combined as a chipset which includes one or more monolithic integrated circuit chips. Referring to FIG. 1, such a chipset can include one or more of the multiplexer 121, analog-to-digital converter 125, processing unit 127 and wireless communication transceiver 141. The chipset can further include one or more components of the sensors 111-114, such as amplifier 213 and output filter 215. Similarly, the components of the sensors 111-114 such as sensor electrode 211, amplifier 213 and output filter 215 can be integrated. It is also possible to integrate components associated with the external computer 147 into the chipset. FIG. 2 is a diagram showing details of one of the sensor circuits 111 depicted in FIG. 1. The sensor unit includes a sensor electrode 211, an amplifier 213 and an output filter 215.

Dry EMG electrodes

Electrodes for measuring biopotentials are extensively used in modern clinical and biomedical applications. These applications include numerous physiological tests including electrocardiography (ECG), electroencephalography (EEG), electrical impedance tomography (EIT), electromyography (EMG) and electro-oculography (EOG). The electrodes for these types of physiological tests function as a transducer by transforming the electrical potentials or biopotentials within the body into an electric voltage that can be measured by conventional measurement and recording devices. One form of dry electrode is a polysiloxane electrode, described by Klaus-Peter Hoffmann, and Roman Ruff, Flexible dry surface-electrodes for ECG long-term monitoring, Proceedings of the 29th Annual International Conference of the IEEE EMBS Cite Internationale, Lyon, France Aug. 23-26, 2007, IEEE Document No. 1-4244-0788-5/07. The described material is based on a medically approved polysiloxane framework (Pt catalyzed) loaded with conductive nano-particles to realize the electronconductive component. To improve the electrode-to-skin impedance a general-purpose electrolyte part was added to provide the ion-conductivity.

In general, most commercial physiological electrodes for these applications today are placed on the surface of the skin. Because of such use, it is important to understand the anatomy of the skin to address the problems encountered with these electrodes. The skin is a layered structure, which includes the epidermis and the dermis. The dermis contains the vascular and nervous components. Further it is the part of the skin where pain has its origins. The epidermis is the most important layer in the electrode/skin interface. The epidermis comprises a number of layers. These layers include: [0114] a) Stratum basale or stratum germinativum, which contains living basal cells, that grow and divide, eventually migrating into the other layers of the epidermis; [0115] b) Stratum spinosum, which contains living cells that have migrated from the stratum basale. The early stages of desmosomes can be found in this layer; [0116] c) Stratum granulosum, which contains cells with many desmosomal connections, forms a waterproof barrier that prevents fluid loss from the body; [0117] d) Stratum lucidum, which is a transition layer between the stratum granulosum and the stratum corneum. It is thickest in high friction areas such as the palms and the soles of the feet; and [0118] e) Stratum corneum, which is the outer layer, contains dry, dead cells, flattened to form a relatively continuous thin outer membrane of skin. The deeper cells of this layer still retain the desmosomal connections, but as they are pushed toward the surface by newly formed cells in the underlying layers, the junctions gradually break and the cells are lost.

The stratum corneum is the primary source of high electrical impedance. This is because dead tissue has different electrical characteristics from live tissue, and has much higher electrical impedance. Thus, this layer dramatically influences the biopotential measurements. The stratum corneum is estimated to be approximately one tenth the thickness of the epidermis except for the palms of the hand and the foot where this layer is much thicker. The stratum corneum, further, is very thin and uniform in most regions of the body surface ranging from 13 to 15.mu.m with a maximum of about 20.mu.m. If the high impedance results from the stratum corneum can be reduced, a more stable electrode will result. Therefore with existing physiological electrodes, the skin is prepared prior to application when lower impedance is required.

Use of Alternative Electrodes Possible

The most common electrode preparation methods that cope with the high impedance effects of the stratum corneum are: 1) shaving the hair from the skin; and either 2a) abrading the stratum corneum or 2b) using an electrolytic gel. The use of an electrolytic gel or fluid is often referred to as "wet" electrodes. Hair is shaved from the skin to improve the contact between the electrodes and the skin surface. The goal of the abrasion of the stratum corneum is to reduce the thickness of (or remove) the stratum corneum (and therefore its electrically insulating characteristics). Drawbacks of abrading the skin are that the abraded area regenerates dead cells fairly quickly (resulting in a limited time period for using the electrode), and if the abrasion is too deep the person can experience pain. Additionally, electrolytic gels or fluids may be applied to abraded surface to enhance the contact. Alternatively, electrolytic gels or fluids can be applied to the surface of the skin directly. The electrolytic gel having a high concentration of conductive ions diffuses into the stratum corneum and improves its conductivity. Drawbacks observed with the use of electrolytic gels or fluids involve the change of conductivity with time as the gels dry, discomfort (an itching sensation) at the patients skin as a result of the gels drying, and the possibility of a rash due to an allergic reaction to the electrolytic gels.

In addition to the inconvenience of "wet" electrodes, "wet" electrodes have other disadvantages. These include the need for skin preparation and stabilization of the electrode with respect to the skin surface. This is because movement of the electrode on the surface of the skin causes the thickness of the electrolytic layer (formed by the electrolytic gels or fluids) to change resulting in false variation in the measured biopotential. Some electrode designs have an adhesive backing and/or grated surfaces to reduce the movement of the electrode on the skin surface; however, neither of these features eliminates completely the movement of the electrode with respect to the subject's skin. Another drawback is the length of time required to prepare the skin and apply the electrolytic gels or fluids prior to measurement of the biopotentials. Nevertheless, it is possible to use "wet" electrodes for sensing hand movement.

A less common type of physiological electrode is a nonpolarizable "dry" electrode. These ceramic, high sodium ion conducting electrodes do not need an electrolytic gel before their application. The recordings using these physiological electrodes are based on a sodium ion exchange between the skin and the electrode. The skin-electrode impedance of these type of electrodes are found to decrease as a function of application time. This is a result of perspiration being produced by the body under the electrode almost immediately after application of the electrode on the skin. Drawbacks, however, are similar to those of "wet" electrodes.

Another less common type of physiological electrode is an active "dry" electrode with an amplifier. Advances in solid-state electronic technology have made it possible to record surface biopotentials utilizing electrodes that can be applied directly to the skin without abrading the skin or using an electrolytic gel. These electrodes are not based on an electrochemical electrode-electrolyte interface. Rather, these electrodes are active and contain a very high impedance-converting amplifier. Some claim that by incorporating the high impedance-converting amplifier into the electrode, biopotentials can be detected with minimal or no distortion. Further information is found in, Babhk Alizadeh-Taheri et al., An Active Microfabricated Scalp Electrode Array for EEG Recording Sensors and Actuators, A54, pp. 606-611, Elsevier Science, S. A. (1996); in, Edward D. Flinn, "Ouch-less Injections", Popular Science, October 1998, p. 33 United States; in, Patrick Griss et al., "Micromachined Electrodes for Biopotential Measurements", Journal of Microelectromechanical Systems, March 2001, pp. 10-16, vol. 10.

EMG Data Acquisition System

Electromyography (EMG) is an electrophysiological technique for evaluating and recording physiological properties of muscles at rest and while contracting. EMG is performed using a device called an electromyograph, to produce a record called an electromyogram. An electromyograph detects the electrical potential generated by muscle cels when these cells contract, and also when the cells are at rest. The electrical source is the muscle membrane potential, about −70 mV. Due to the applied method the resulting measured potentials range between less than about 50.mu.V to about 20 to about 30 mV. Amplitudes of EMG signal range between 0 to 10 mV (peak-to-peak), or 0 to 1.5 mV (rms). The frequency of the EMG signal is between 0 to 500 Hz. The usable energy of EMG signal is dominant between 50-150 Hz.

EMG data are routinely acquired in clinical and laboratory settings. The details of these procedures can be found in the works of Carlo Deluca, among others. Further information is found in, De Luca, C. J. Electromyography; and in, Encyclopedia of Medical Devices and Instrumentation, (John G. Webster, Ed.) John Wiley Publisher, 98-109 (2006).

The following factors should be considered:

Boost signal to TTL standard level (±5 V.), Noise/Artifact problem, Filter, stability of electrodes attached to skin, proper grounding, DC offset or bias problem that requires Bias adjustment.

The following are EMG measurement stages:

Hand->Preamplifier->RC Filter->Amplifier with Bias Adjustment->A/D Converter->EMG Capture Program.

Analyses of EMG Modulations and Interactions

Reconstruction of controlled hand movement patterns from the EMGs may be conducted in two steps. During the first step an appropriate mathematical algorithm is trained. This training involves adjusting the algorithm parameters. This step is often referred to as "fitting". During the second step, the parameters of the algorithm are fixed, and predictions are produced from a new segment of EMG records.

Some attempts to reconstruct behavioral variables from muscle activity were described in, Lebedev M A, Nicolelis M A., "Brain-Machine Interfaces: Past, Present and Future", Trends Neurosci. 2006 September; 29(9):536-46. Epub 2006 Jul. 21 Review. The performance of the linear model that predicts the parameters of interest as a weighted linear combination of input signals:

$$V(t) = b + \sum_{\tau=-m}^{n} w(\tau)n(t+\tau) + \varepsilon(t)$$

where $n(t+\tau)$ is a vector of input signals (EMG), at time t and time-lag $\tau$ (negative lags correspond to past events), V is the parameter of interest at time t, $w(\tau)$ is a vector of weights for each input at time-lag $\tau$, b is the y-intercept, and $\epsilon(t)$ is the residual error. This equation is solved using linear least squares regression.

To obtain predictions, EMG signals will be full-wave rectified and band-pass filtered in the range of 0.2-20 Hz, A sample number of time lags with temporary time spacing are used, for example 10 time-lags preceding the measurement with temporally spaced at 20-100 ms. The quality of predictions obtained using the EMGs of different muscles will be evaluated by calculating predictions for individual muscles and several muscles in different combinations. 5-10 minutes of data will be used to fit the model and find the weights, $w(\tau)$.

The X and Y coordinates of the writing instrument are first predicted and fit to the writing instrument while the subjects make handnotes. Predictions will be calculated for a different 5-10 minute epoch. The quality of predictions will be evaluated as the eucledian distance between the actual and predicted traces of the writing instrument. Further information is found in, Kim H K, Biggs S J, Schloerb D W, Carmena J M, Lebedev M A, Nicolelis M A, Srinivasan M A., "Continuous Shared Control for Stabilizing Reaching and Grasping with Brain-Machine Interfaces", *IEEE Trans Biomed Eng.* 2006 June; 53(6):1164-73.

As discussed, other pattern recognition computer algorithms may also be applied in any combination.

Further Sensed Data

The human hand is a complex system, with the large number of degrees of freedom, somatosensory receptors embedded in its structure, actuators and tendons, and a complex hierarchical control. Despite this complexity, the user can carry out the different movements virtually effortlessly (after an appropriate and lengthy training). Scientists and engineers made a lot of effort to replicate a sensory-motor function of the human hand, a complex and adaptive system capable of both delicate and precise manipulation and power grasping of heavy objects. Most of these efforts were spent in the area of prosthetic devices and rehabilitation techniques. These efforts led to much greater understanding of general EMG applications. Further information is found in, M. Zecca, S, Micera, M. C. Carrozza, & P. Dario, "Control of Multifunctional Prosthetic Hands by Processing the Electromyographic Signal", *Critical Reviews in Biomedical Engineering,* 30(4-6):459-485 (2002).

Fundamental insights into how arrays of neurons encode motor or sensory variables can be gained from computational methods that attempt to reconstruct or predict aspects of animal behavior or sensory stimuli from the recorded activity of neural populations. The accuracy with which a behavior such as the direction of limb movement or the path of an animal navigating a maze can be reconstructed provides an estimate of the amount of behaviorally relevant information represented in the discharge of the recorded neurons. It should also be possible to invert this process to predict neural activity from behavior. One application of such an approach would be to identify the patterns of neuromuscular activity across a population of muscles needed to elicit desired movements in paralyzed individuals using functional electrical stimulation. Further information is found in, Robert E. Kass, Valerie Ventura and Emery N. Brown, "Statistical Issues in the Analysis of Neuronal Data", J Neurophysiol 94:8-25, 2005. doi:10.1152/jn.00648.2004; in, R. M. Davies, G. L. Gerstein and S. N. Baker, "Measurement of Time-Dependent Changes in the Irregularity of Neural Spiking", J Neurophysiol, Aug. 1, 2006; 96 (2): 906-918; in, Robert E. Kass, Vale rie Ventura, and Emery N. Brown, "Statistical Issues in the Analysis of Neuronal Data", J Neurophysiol 94: 8-25, 2005; doi:10.1152/jn.00648.2004; and in, Nicolelis M A L, Ghazanfar A A, Stambaugh C R, Oliveira L M O, Laubach M, Chapin J K, Nelson R J, Kaas J H, "Simultaneous Encoding of Tactile Information by Three Primate Cortical Areas", Nat Neurosci 1:621-630 (1998).

Functional electrical stimulation involves artificial activation of paralyzed muscles with electrodes and has been used successfully to improve the ability of quadriplegics to perform activities for daily living. The range of motor behaviors that can be generated by functional electrical stimulation, however, is limited to a relatively small set of movements, such as hand grasp and lateral and palmer pinch. A broader range of movements has not been implemented primarily because of the substantial challenge associated with identification of the patterns of muscle stimulation needed to elicit specified movements. Most limb movements, even those involving a single digit, require intricate coordination among multiple muscles that act across several joints. Such complex mechanical systems do not readily lend themselves to deterministic solutions. Although EMG signals recorded from able-bodied subjects can be used to identify patterns of muscle activity associated with a particular movement, this painstaking method yields control signals appropriate only for the motor task from which the EMG signals were originally recorded. In an attempt to overcome this limitation it is possible to use Bayes' theorem to predict the patterns of muscle stimulation needed to produce, in theory, an unlimited set of movements across multiple joints. The bidirectionality of Bayes' theorem facilitated the inverse prediction of neuromuscular activity from behavior. Further information is found in, Heather M. Seifert and Andrew J. Fuglevand, "Restoration of Movement Using Functional Electrical Stimulation and Bayes' Theorem", The Journal of Neuroscience, Nov. 1, 2002, 22(21):9465-9474.

Functional Implementation

Figure 4:
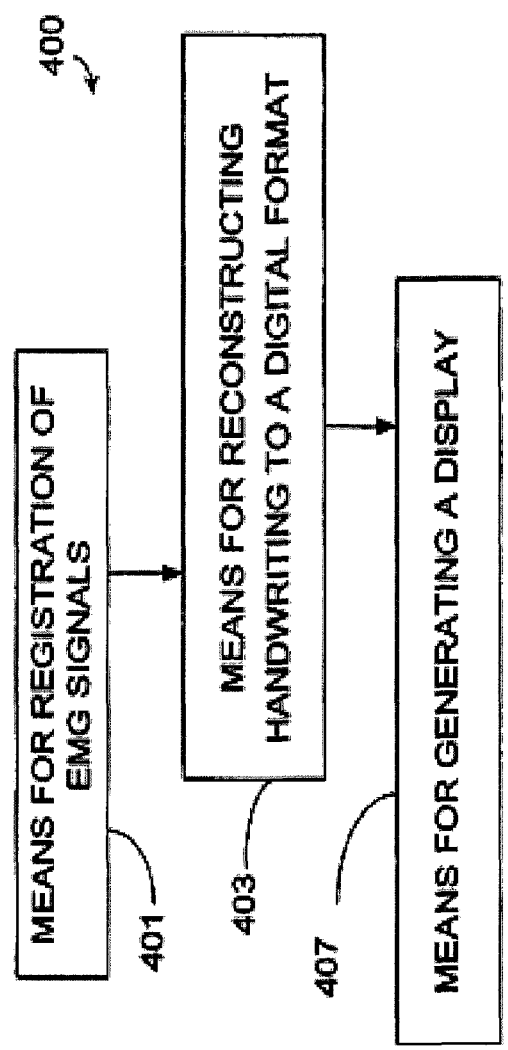
FIG. 4 is a diagram depicting a functional implementation of a system to record a handwriting activity.

FIG. 4 is a diagram depicting a functional implementation of a system 400 to record a handwriting activity. The system includes means 401 for registration of electromyography (EMG) signals from one or more muscles at selected locations, which may include the sensors 111-114 (FIG. 1) as well as the remaining components of the circuit 100 used to sense EMG data. The means 401 for registration of EMG signals may comprise sensors, electrodes, amplifiers, bandpass filters, multiplexer, analog to digital converter, processing unit, and the means for registration of EMG signals may provide a routine to improve signal to noise ratio. Also included are means 403 for reconstructing handwriting to a digital format from the EMG signals, depicted as computer 147 (FIG. 1), although some or all of these functions can be provided by processor 127. The digital format includes both a visual representation of the reconstructed handwriting and a digitized rendition, such as text. The system 400 includes means 407 for generating a display corresponding to the digital format, depicted as computer 147 (FIG. 1).

The means 403, 407 for reconstructing and for generating a display corresponding to the digital format can generate a display of machine-editable text corresponding to the digital format and in the case of a drawing generate the drawing in an editable format.

Some configurations enhance the interaction of sensed EMG signals with creation of handwriting images and computer recognition of handwriting. There are various modifications that can be made, including using the EMG signals directly in the recognition of handwriting, "training" and "learning" of a computer application for recognition of handwriting, and the use of shorthand/or shortcuts for transcription purposes.

Figure 5:
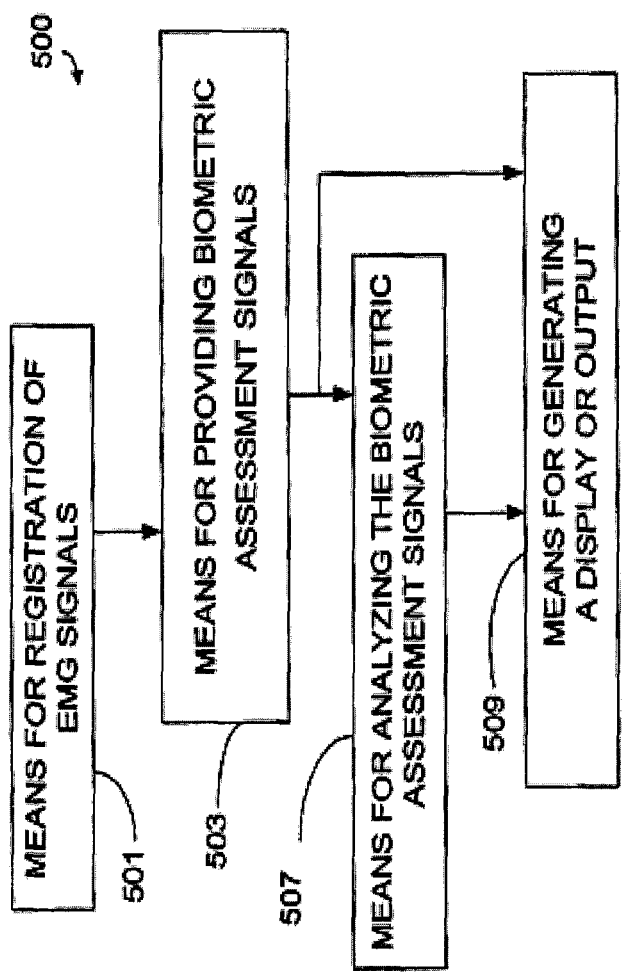
FIG. 5 is a diagram depicting a functional implementation of a system to generate a biometric assessment based on controlled hand movement.

FIG. 5 is a diagram depicting a functional implementation of a system 500 to perform biometric assessment. The system generally follows the structure of the system used to perform handwriting analysis (FIG. 4), and may use handwriting as a form of controlled hand movement. The system includes means 501 for registration of electromyography (EMG) signals from one or more muscles at selected locations, which may include the sensors 111-114 (FIG. 1) as well as the remaining components of the circuit 100 used to sense EMG data. The means 501 for registration of EMG signals may comprise sensors, electrodes, amplifiers, bandpass filters, multiplexer, analog to digital converter, processing unit, and the means for registration of EMG signals may provide a routine to improve signal to noise ratio. Also included are means 503 for providing biometric assessment signals from the EMG signals, depicted as computer 147 (FIG. 1). The biometric assessment signals can then be analyzed, for example using computer 147, and some or all of these functions can be provided by processor 127. The system 500 includes means 507 for analyzing the biometric assessment signals, and means 509 for generating a display or output corresponding to the digital format, depicted as computer 157 (FIG. 1).

The means 503, 507, 509 for performing biometric analysis and for generating a display corresponding to the digital format can further analyze the biometric assessment signals to provide data or interpretation of data, or biometric assessment signals can be read externally.

The invention includes an approach for synchronizing recordings of EEG, EMG, and handwriting traces using trials in such way that EEG and EMG data is synchronized according to a press down signal made by a pen or stylus on a tablet that digitizes handwriting traces. A digitizer of handwriting traces can be a tablet, or any other system that captures handwriting traces in a digital format. The inventors discovered that with this approach that recordings for control (healthy, non-PD) patients have different correlations characteristics for EMG and EEG signals compared to PD patients. Control and PD patients were tested by making repeated writings of a single character or number, e.g. "3". Both, EEG and EMG data flows were synchronized with the digitizer of handwriting traces. In particular, the inventors also discovered four biomarker as follows:

1. Control patients had EMG signals with defined short burst of high intensities. PD patients had EMG signals with evenly distributed intensities without distinctive short bursts.
2. Control patients demonstrated a relatively high correlation between two EMG signals from channels on hand muscles. PD patients had low correlations for the same channels.
3. In patients with Parkinson's disease we observed a growth of correlations in cortex areas activated during handwriting
4. Control patients had EEG signals with correlations that lasted for short time intervals. PD patients had EEG signals with correlations which endured over longer time intervals.

We believe the biomarkers can be used in systems, devices and a methods for detecting, analyzing or treating neurological disorders. We have discovered and claim two types of devices. One device uses off-the-shelf equipment and suitable software for data acquisition and synchronization of data from multiple channels. Another device used dedicated hardware and software for data acquisition and synchronization.

Both devices, used either alone or in combination, are beneficial for diagnosis not only Parkinson's Disease (PD), but also other neurodegenerative diseases such as Essential Tremor Disorder, Alzheimer's disease, Multiple Sclerosis, Encephalitis, Meningitis, Tropical Spastic Paraparesis, Arachnoid Cysts, Huntington's, Locked-In Syndrome, and Tourette's. In a similar manner, the methods and apparatus disclosed herein may also be useful to acquire feedback for deep brain stimulation and brain surgeries. Today such procedures are done relatively blindly by surgeons and may require one or more post-operative adjustments. However, our methods and apparatus provide objective measurements that may enable a surgeon, physician, researcher or clinician to gain insight into the efficacy of the deep brain stimulation or surgery.

Laboratory Setup

Handwriting [1] provides an excellent methodological tool for quantitative studies of statistical and correlation properties of bio-signals. First, it consists of stereotyped hand movements that involve two basic motor components: firmly holding a pen by the fingers and moving the hand and the fingers to produce written text. Second, handwriting is tracked using a laboratory setup with a pen or stylus and a digitizing tablet which allows one to compare handwriting trials, which are well synchronized with respect to each other. Such compatibility synchronization of time-dependent data is crucial for trial-to-trial statistical and correlation analysis.

Figure 6:
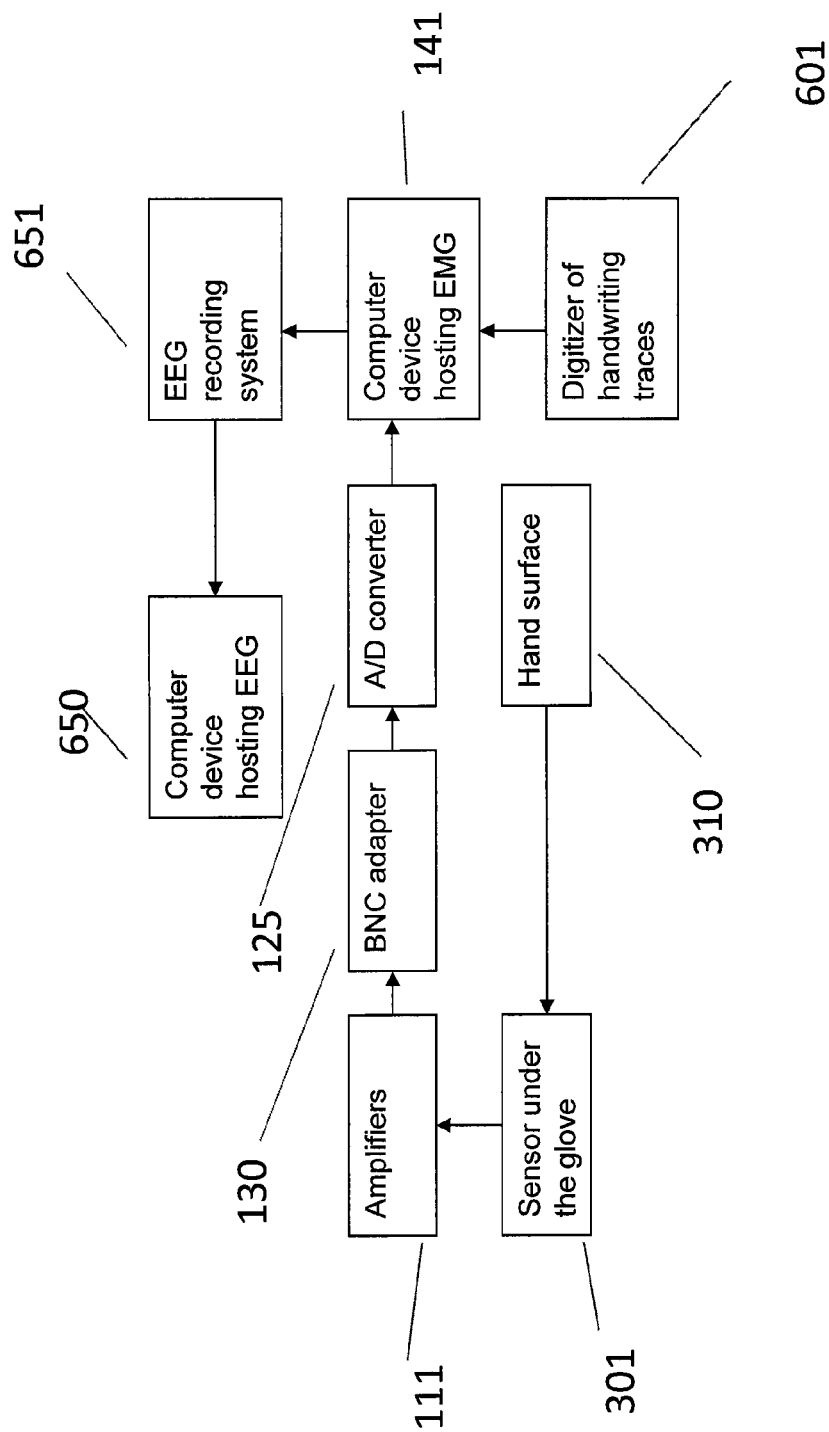
FIG. 6 is a high level schematic view of the laboratory set up used to identify biomarkers.
Figure 8:
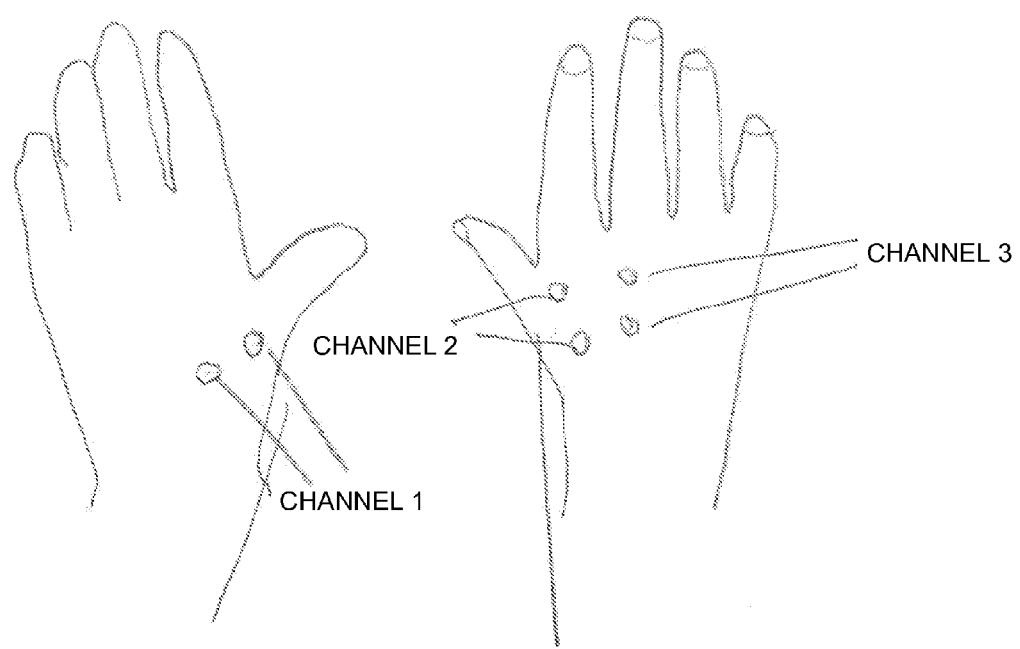
FIG. 8 is a view of the gloves and channels used for the laboratory set up and the embodiment of the invention shown in FIGS. 6 and 7.

FIG. 6 shows the block diagram of the laboratory system which relied upon an off-the-shelf EEG system and a commercial digitizer 310. It included a LogiManage digitizer 601 for digitizing handwriting traces that produced X and Y coordinates, as well as "press on paper" signal. EEG signals were recorded on a dedicated computer 650, which was connected to an EEG recording system 651 via a printer cable. The data from EEG recording system was saved in files on EEG dedicated computer 650. The EMG signals were taken from a glove 301 that was equipped with sensors as shown in FIG. 8. The sensor circuits 111 detected and amplified the signals. The sensor circuits were connected by a BNC adapter 130 to an A/D converter 124. The EMG signals were amplified and then converted into digital signals by the Analog to Digital Converter (ADC) 124 which was connected to an EMG dedicated computer 141 via one of the computer's USB port. The ADC 124 converts the real world subject and patient biometric signals into biometric signal data that may be input to and stored in the memory of a computer. The computer 141 had software for implementing the steps shown in FIGS. 4 and 5. The subjects wrote the number "3" on the digitizer 601. The start and finish of each event was detected by the Pen Down and Pen Up output signals of the digitizer 601. The EEG files and the EMG files were synchronized with the Pen Down and Pen Up output signals and their time stamps that we used to determine the trial intervals.

An EEG recording system 651 was used to sense, capture, and record EEG signals. Such EEG recording systems are commercially available from a number of suppliers in many configurations. For example, Brain Products, in Munich, Germany makes and sells systems which capture EEG signals in 64 channels. Their systems include a cap with 64 or more sensors and recorders that have suitable software to receive the EEG signals from the sensors and simultaneously record them. Another EEG system supplier is EGI, with offices at 1600 Millrace Drive, Suite 307, Eugene, Oreg. 97403. EGI makes the Geodesic brand of EEG systems. Their systems may record 128-256 channels of EEG information.

The EEG signals are synchronized with the EMG signals using the Pen Down and Pen Up output signals of the digitizer 601. The digitizer signals are input to EMG computer 141 and then output to EEG recording system 651. As an alternative, the digitizer signals may be directly connected to EEG recording system 651 or to the EEG computer 650. In operation, the Pen Down and Pen Up digitizer signals mark the beginning and the end of one event where the subject writes the letter "3" or an equivalent character or characters including and not limited to numbers, letters, symbols or groups thereof. The character or groups of characters are selected to have definite starting and stopping points and are normally written with the pen in continuous contact with the digitizer.

EEG and EMG Systems

Based upon the successful results of experiments with the off-the-shelf EEG system, we determined it would be feasible to make a dedicated system that included EEG and EMG sensors, hardware and software. FIG. 7A shows a version of a data acquisition system that contains a microprocessor-based EMG and EEG data acquisition systems 710, 720 that send EMG and EEG data streams wirelessly via antenna 740 to a host computer 750 having an antenna 752. The host computer 750 is connected to a digitizer 601 of handwriting traces via a USB connector. Microcontroller 730 is programmed to synchronize EEG and EMG data streams. Such programming within the ordinary capabilities of one skilled in the art. The EEG and EMG signals are time stamped and the Pen Down event is sensed by a digitizer. Each trial begins with a Pen Down event and ends with a Pen Up event. The Pen Down event is used to synchronize the EEG and EMG channels. The host computer receives the simultaneous EEG and EMG signals. After a user presses down a pen, a Pen Down signal is included in the EEG and EMG files and is used to distinguish sequential trials for each other. A trial is a time period, during which an individual character is analyzed. In operation, the host receives the data streams from the EMG and EEG systems. If the microcontroller does not directly synchronize the two steams, then the host may use the signals from the digitizer 601 to time stamp both EMG and EEG data streams.

We used a commercially available apparatus known as a LogiPen device with a digitizer tablet to record handwriting traces. EMGs were sampled with bipolar surface EMG electrodes (Kendall Arbo). Our multi-channel EMG laboratory system of FIG. 6 consisted of the amplifiers powered by one 9 V battery and National Instruments digitizer NI 9215 with the sample rate of 1000 Hz. Handwriting and EMG inputs were synchronized by a LabVIEW data acquisition program based on Pen Down events. EMGs of several hand muscles were simultaneously recorded. In the system consisting of differential channels (FIG. 8), one pair of electrodes 810 sampled EMG activity from flexor pollicis brevis and abductor pollicis brevis. The second pair of electrodes 812 recorded from the first dorsal interesseus, and the third from the second and third dorsal interosseus muscles.

We used commercially available tablet such as the LogiManage band tablet as a digitizer of handwriting traces for producing X and Y coordinates, as well as a "press on paper" signal. EMG signals were recorded on a dedicated computer 141, which was connected to an EEG recording system 651 via a printer cable. The data from EEG recording system was saved in files on EEG dedicated computer 650. These files also contained the "press on paper" signals and their time stamps that we used to determine the trial intervals. Analog to Digital Converter (A/DC) 125 was connected to the EEG computer 141 via a USB port. A BNC adapter 130 is needed because off the shelf Analog to Digital Converters usually require USB types of input connectors, but analog outputs are different.

Each of the computers has a processor, memory, a visual display, input and output ports including USB ports and ports for sending and receiving data wirelessly via such protocols as Bluetooth. The A/D converter samples the real-time EMG or EEG signals at selected times and stores the value of each sampled signals a biometric data signal. The time of occurrence of the biometric data signal is also stored with the data for later analysis. The memory of the computer includes random access memory and read only memory. Software and data are stored in the memory. Software includes operating system software and application software for processing data. In particular, the software includes one or more modules with the ability to process the signal data in accordance with the algorithms disclosed herein to generate the Pearson correlation coefficients. One the data is processed, the operator of the computer may then use the graphical software to display stored subject and stored patient biometric data signals on the computer display. As an alternative, the computer may include further hardware or software or both to automatically compare patient signal data to the subject stored data and output a signal or other indicia that the biomarker for a disorder is likely present or not.

The patient uses a stylus or pen to write the same character or characters on a digitizing tablet 601. The tablet 610 is coupled to the computer 141. The tablet generates time-based The patient uses a stylus or pen to write the same character or characters on a digitizing tablet 601. The tablet 610 is coupled to the computer 141. The tablet generates time-based digital signals of X and Y coordinates of the patient's handwriting. Those time-based signals are synchronized with the EMG signals data by a synchronizing software module. Other software modules process signal data representative of repeated identical handwriting samples to generate templates of the average intensity of the EMG signals over time and to generate Pearson correlation coefficients between two or more streams of EEG signals. The results of typical software processing are shown in FIGS. 9-12.

Those time-based signals are synchronized with the EMG signals data by a synchronizing software module. Other software modules process signal data representative of repeated identical handwriting samples to generate templates of the average intensity of the EMG signals over time and to generate Pearson correlation coefficients between two or more streams of EEG signals. The results of typical software processing are shown in FIGS. 9-12.

The patient's head is covered with an EEG cap which generates 64 channels of EEG signals. Those signals are also synchronized with the time-based X-Y coordinate data signals for the digitizer. An EEG data processing software module processes the EEG signals to calculate the Pearson coefficient correlations during the handwriting samples and generate the correlation graphs shown in FIGS. 22-14-18 and 22-25.

Figure 7B:
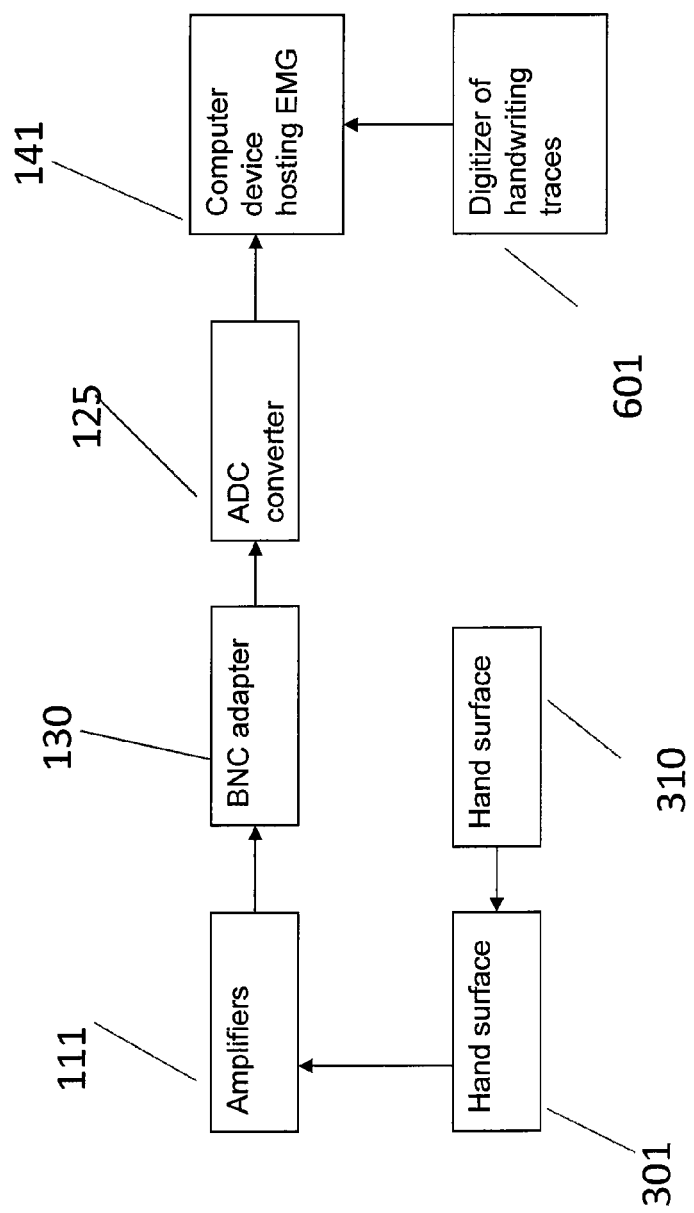
FIG. 7B is a high level schematic view of an EEG only embodiment of the invention.

A third embodiment of our invention as shown in FIG. 7B relies only on EMG signals. It is similar to the systems shown above in FIGS. 6 and 7 except that the EEG sensors and recording equipment and apparatus are omitted. The embodiment of FIG. 7B uses the glove 301 to generate two or more channels of EMG signals. The signals are amplified and converted by ADC 125 into streams of biometric signals data corresponding to the EMG signals generated during handwriting. The patient uses a stylus or pen to write the same character or characters on a digitizing tablet 601. The tablet 610 is coupled to the computer 141. The tablet generates time-based digital signals of X and Y coordinates of the patient's handwriting. Those time-based signals are synchronized with the EMG signals data by a synchronizing software module. Other software modules process signal data representative of repeated identical handwriting samples to generate templates of the average intensity of the EMG signals over time and to generate Pearson correlation coefficients between two or more streams of EEG signals. The results of typical software processing are shown in FIGS. 9-12.

Software and Algorithm Development

The purpose and function of data acquisition software is to acquire sensor data and synchronize the data from multiple sensors. Such synchronization may be achieved different ways depending upon the hardware devices, their operating systems and the host computer operating system. Those skilled in the art understand that different hardware may require different software, but the task of synchronizing is the same and may be achieved without inventive effort. The data analysis software relies upon data acquisition software that is written in LabVIEW and saved in MATLAB format. Another program also written in MATLAB format reads those files and analyzes them.

Application software in computer stores patient biometric signals as biometric signal data in the computer memory. Software also processes patient biometric signal data and generates generating graphic representations of the stored biometric signal data for the healthy subject and for the patient Further software presents on the visual display graphic representations of the healthy subject and the patient to enable a viewer to compare characteristics of the data.

LabVIEW is the trade name for suite of software products supplied by National Instruments. It provides a graphical programming environment used by engineers and scientists to develop sophisticated measurement, test, and control systems using intuitive graphical icons and wires that resemble a flowchart. It offers integration with thousands of hardware devices and provides hundreds of built-in libraries for advanced analysis and data visualization—all for creating virtual instrumentation. The LabVIEW platform is scalable across multiple targets and operating systems.

MATLAB is a trade name describing a suite of computer programs offered by The MathWorks, Inc. of Natick, Mass. MATLAB® software provides a high-level technical computing language and interactive software for algorithm development, data visualization, data analysis, and numerical computation. Using MATLAB, scientists and engineers can solve technical computing problems faster than with traditional programming languages, such as C, C++, and Fortran. MATLAB may be used in a wide range of applications, including signal and image processing, communications, control design, test and measurement, financial modeling and analysis, and computational biology. A number of add-on toolboxes (collections of special-purpose MATLAB functions) extend the MATLAB environment to solve particular classes of problems in these application areas. MATLAB can integrate its code with other languages and applications, and distribute MATLAB algorithms and applications.

The foregoing software tools were used for data acquisition, analysis, computation of values, such as Pearson coefficients, and display of results. The detailed algorithms described in this patent show one skilled in the art how the data acquired by the data acquisition software is processed in by MATLAB or an equivalent program. As such, it is sufficient for those skilled in the art to have examples of data acquisition software since they are expected to be familiar with using LabVIEW and MATLAB programs or their equivalents and will be able to adapt such software to execute the algorithms disclosed herein.

Software synchronizes EEG and EMG signals with respect to each other according to press down signal from the digitizer of handwriting traces. Handwriting trials are defined as the epochs starting 500 ms before the pen touches a paper and ending 1000 ms after this moment of time. The amplitudes of EMG and EEG signals, $A_{emg}$ and $A_{eeg}$ is squared to get the signal "intensity", $I_{emg}=A_{emg}^2$ and $I_{eeg}=A_{eeg}^2$.

To study time-dependent statistical and correlation properties of EMG and EEG signals, 1500-ms trials are subdivided into 15 time intervals, each with the duration of 100 ms, and the signal "energy" is calculated for each of 15 intervals as the sum, $$E_{emg(eeg)}(n, \alpha, j) = \sum_{interval} I_{emg(eeg)}(n, \alpha, j) \quad (1)$$

where n=1÷15, a=1÷3, j=1÷N (where N is the total number of trials), enumerate the time intervals, recording channels, and trials, respectively. To obtain dimensionless variables for each interval, the energies $E_{emg(eeg)}(n, \alpha, j)$ are normalized by dividing by the corresponding mean values, $E^{mean}_{emg(eeg)}(n, \alpha) = \langle (E_{emg(eeg)}(n, \alpha, j) \rangle$. Here and hereafter $\langle \ldots \rangle$ stands for averaging over trials, $$\langle \ldots \rangle = \frac{1}{N} \sum_{j=1}^{j=N} \ldots \quad (2)$$

Thus, in our analysis EMG and EEG signals for each recording channel are characterized by the logarithms of dimensionless energies $$\varepsilon_{emg(eeg)}(n, \alpha, j) = \frac{E_{emg(eeg)}(n, \alpha, j)}{E^{mean}_{emg(eeg)}(n, \alpha)} \quad (3)$$

We have found [2] that trial-to-trial distribution of values $\epsilon_{emg(eeg)}$ is well described by log-normal distribution [3]. Therefore, we compute the logarithms of the dimensionless energies as follows:

$$L_{emg}(n,a,j) = \log[\epsilon_{emg}(n,\alpha,j)] \text{ and } L_{eeg}(n,\alpha,j) = \log[\epsilon_{eeg}(n,\alpha,j)] \quad (4)$$

and Pearson correlation coefficients defined as $$P_{emg}(n, m, \alpha, \beta) = \frac{\langle (L_{emg}(n, \alpha, j) - \langle L_{emg}(n, \alpha, j) \rangle)(L_{emg}(m, \beta, j) - \langle L_{emg}(m, \beta, j) \rangle) \rangle}{S_{emg}(n, \alpha) S_{emg}(m, \beta)} \quad (5a)$$

$$P_{eeg}(n, m, \alpha, \beta) = \frac{\langle (L_{eeg}(n, \alpha, j) - \langle L_{eeg}(n, \alpha, j) \rangle)(L_{eeg}(m, \beta, j) - \langle L_{eeg}(m, \beta, j) \rangle) \rangle}{S_{eeg}(n, \alpha) S_{eeg}(m, \beta)} \quad (5b)$$

where $S_{emg(eeg)}$ are the standard deviations of the functions $L_{emg}(n, \alpha, j)$ and $L_{eeg}(n, \alpha, j)$, respectively. Since the values $L_{emg(eeg)}$ are normally distributed over trials, one can compute not only the correlation coefficients but also the confidence interval, or, in other words, the upper and lower limits of a correlation coefficient magnitude, which contains the magnitude with the probability of 95% (or p-value=0.95). Owing to the definitions (5), the modulus of Pearson coefficients does not exceed 1.

Parkinson Disease Biomarkers

Statistical and correlation properties of recorded EMG and EEG signals were studied by using the above-described algorithms. These studies resulted in several visible biomarkers of Parkinson disease which we list and discuss below.

Deterioration of EMG Signals Templates

Figure 9:
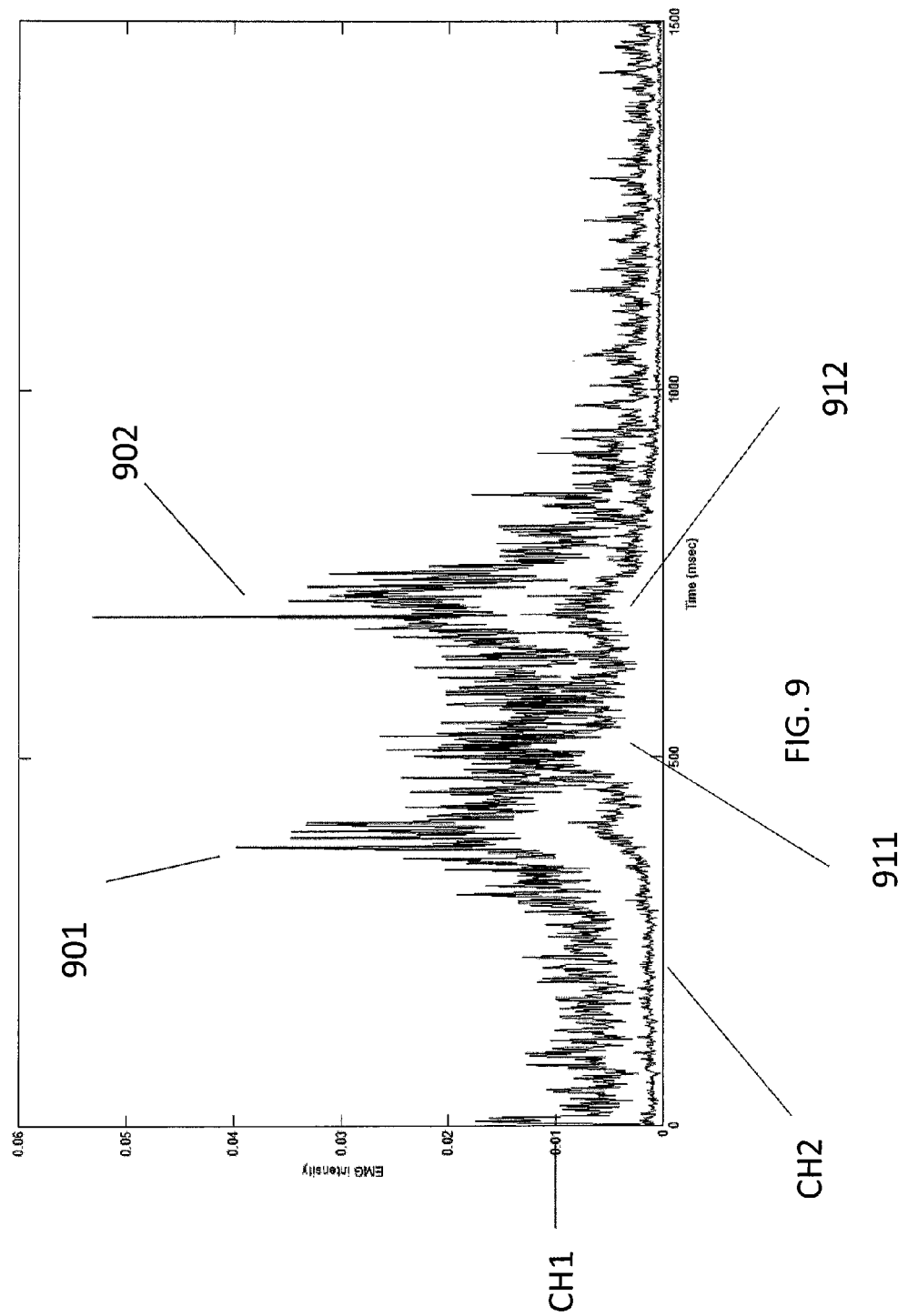
FIG. 9 is a graphic representation of a template of EMG intensity of EMG in two channels for control healthy subject.
Figure 10:
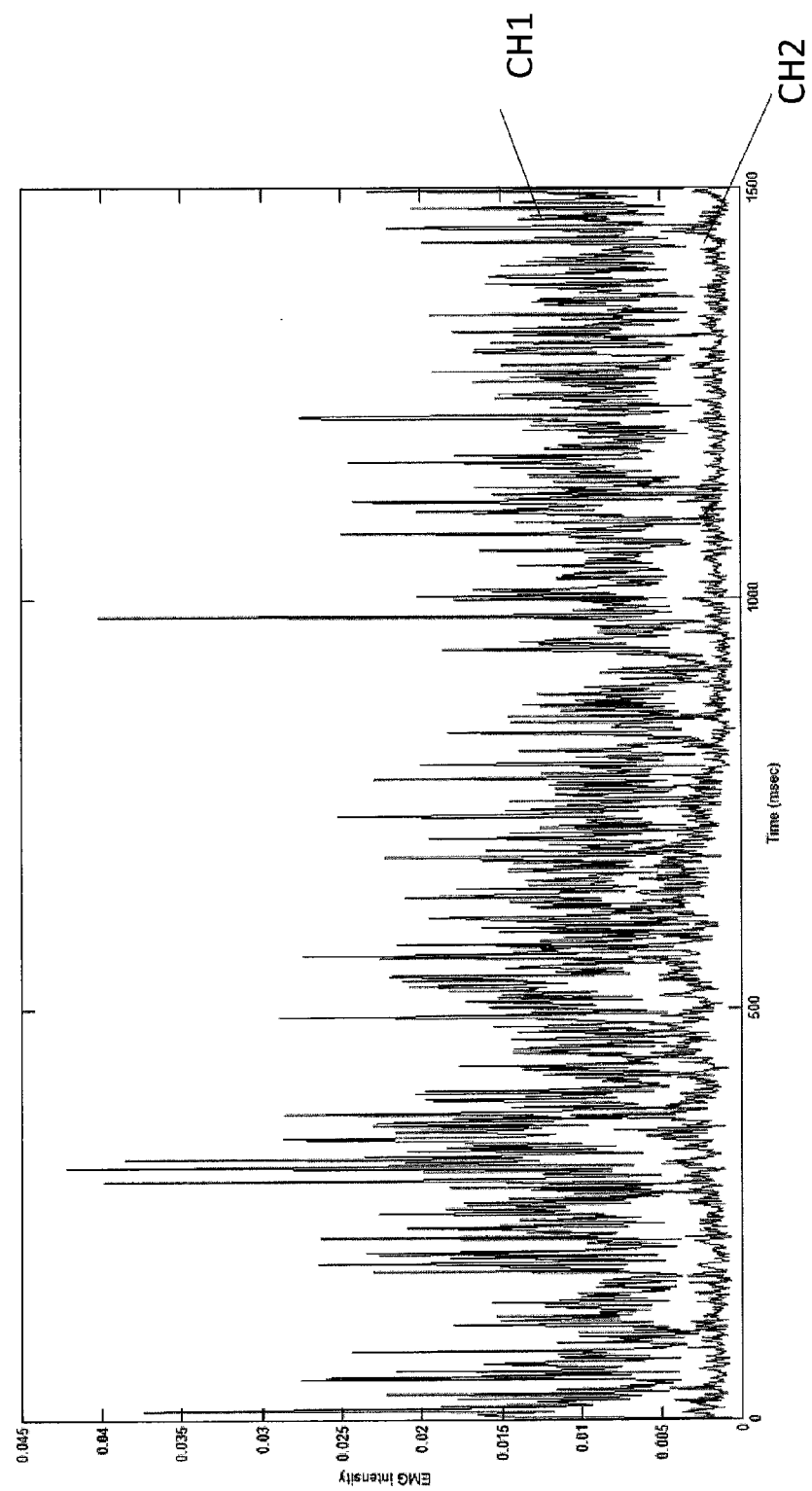
FIG. 10 is a graphic representation of a template of EMG intensity of EMG in two channels for a PD patient.

First, we computed so-called EMG templates, which are defined as trial-average intensity of EMG signals, $I(n, \alpha) = \langle (I_{emg}(n, \alpha, j) \rangle$. In FIG. 9 we show a typical template computed for EMG signals in two different channels of a control healthy subject. FIG. 10 represents a template computed for a PD patient. Both templates show the average intensities computed for 40 trials of handwriting of digit "3". The point t=500 ms corresponds to the moment of time when a pen touches a paper the first time. It is readily seen that the template of control subject of FIG. 9 has well determined bursts corresponding to handwriting itself, while EMG intensity in the vicinity where a subject is only firmly holding a pen by the fingers is much lower. In the case of results for a PD patient as shown in FIG. 10, the EMG intensity is almost homogeneously distributed over the whole epoch, corresponding both to firmly holding a pen by the fingers and to moving the hand and the fingers to produce written text.

Changes of Pearson Correlation Coefficients Between Different EMG Channels

Figure 11:
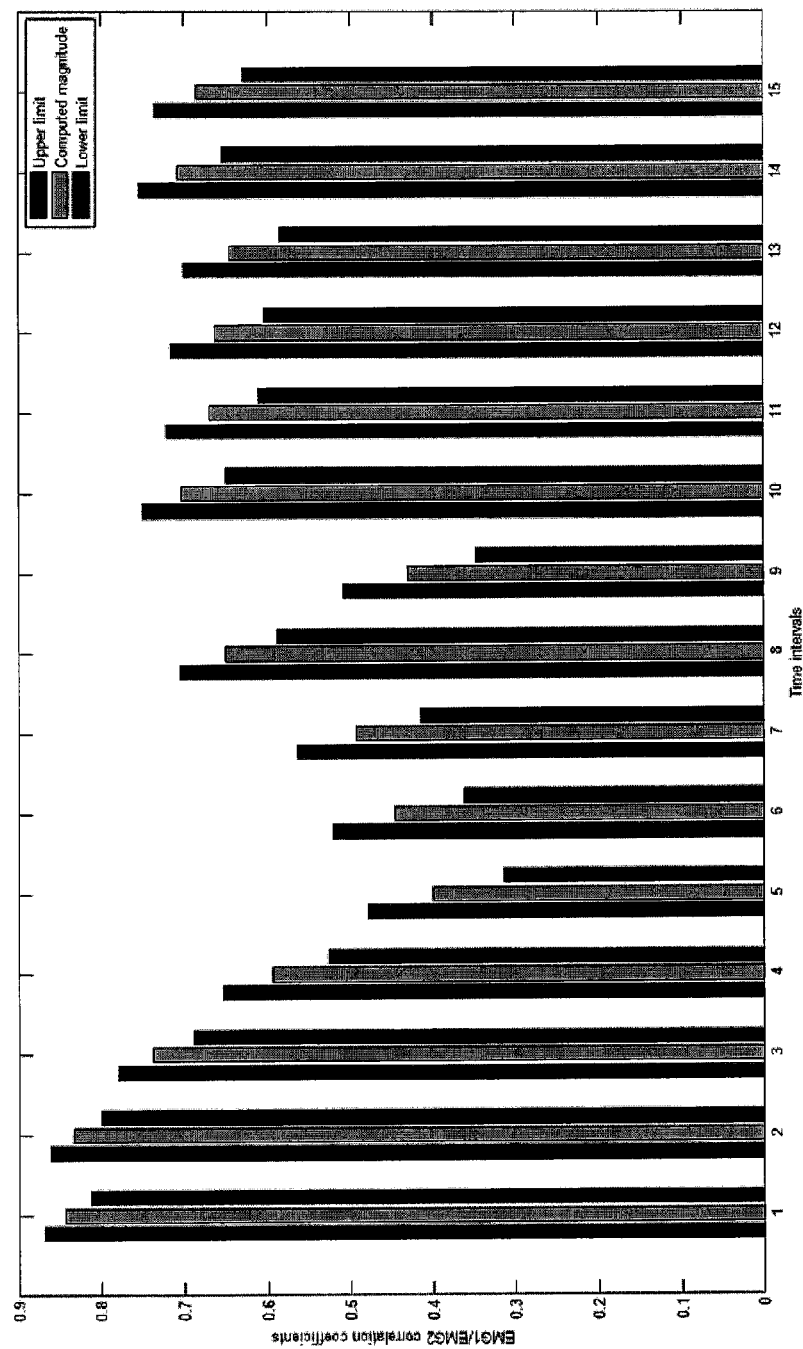
FIG. 11 is a graphic representation of timed behavior of Pearson correlation coefficient (center bar) for EMG signals recorded in two different channels (EMG1 and EMG2) for a healthy control subject.
Figure 12:
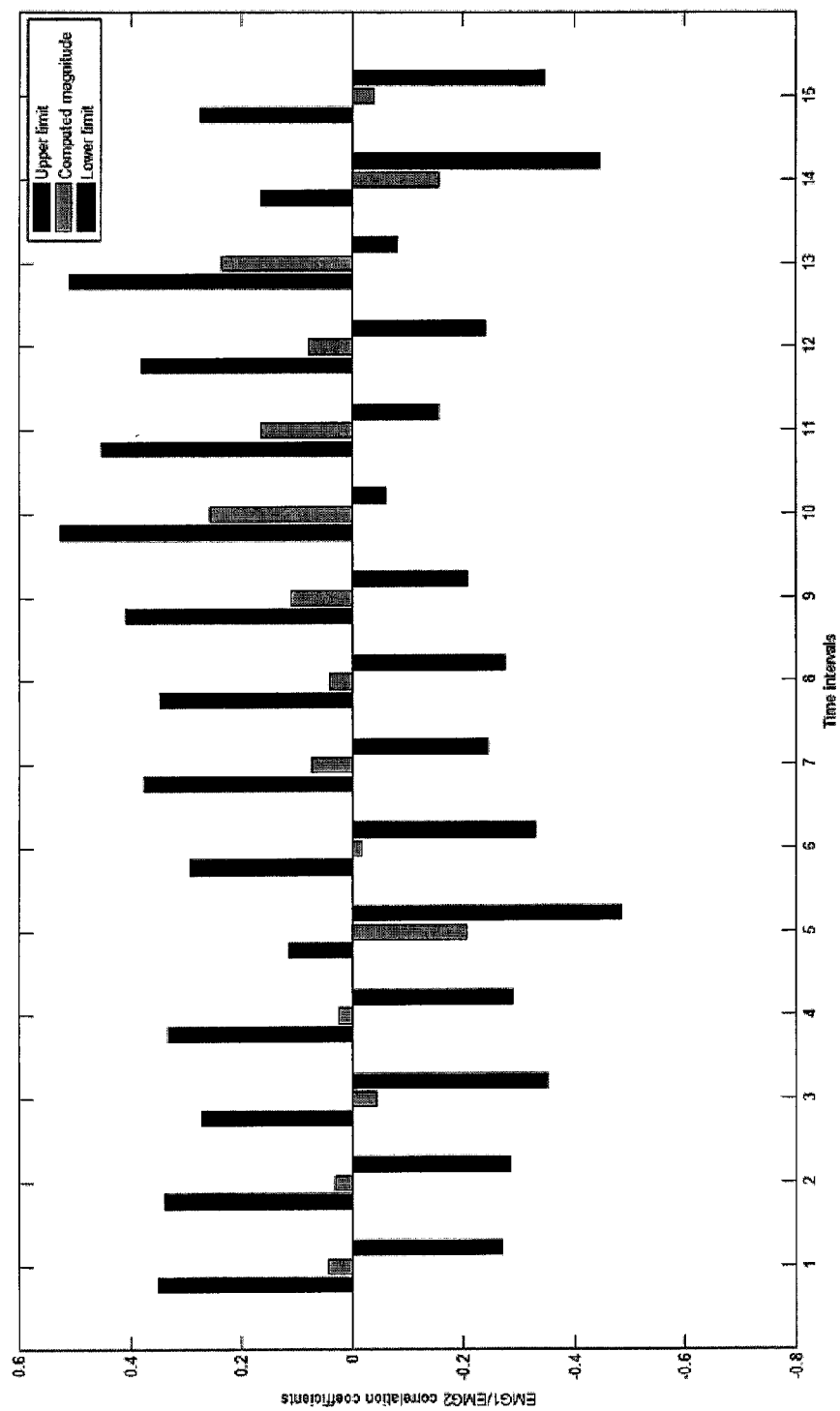
FIG. 12 is a graphic representation of timed behavior of Pearson correlation coefficient (center bar) for EMG signals recorded in two different channels (EMG1 and EMG2) for a PD patient.

Next, we compare Pearson correlation coefficients of control and PD subjects computed between two EMG channels. FIG. 11 shows time behavior of the Pearson correlation coefficients for a healthy control subject. There the center bars represent a computed magnitude of the coefficient, while the left and right bars represent the upper and lower limits, respectively. Thus, with the probability 95% a real magnitude of the coefficient lies between the magnitudes shown by the left and right bars.

We observed quite a high correlation between EMG signals (EMG1 and EMG2) recorded from two groups of hand muscles, involved in handwriting, in all 15 time intervals. Here the interval 6 corresponds to the first 100 ms after a pen touches a digital paper. For the PD patient we did not observe a proper correlation between these two different hand-muscle groups. Correlation is practically absent in all time intervals as easily seen in FIG. 12.

Growth of Cortex Areas Activated During Handwriting

Figure 13:
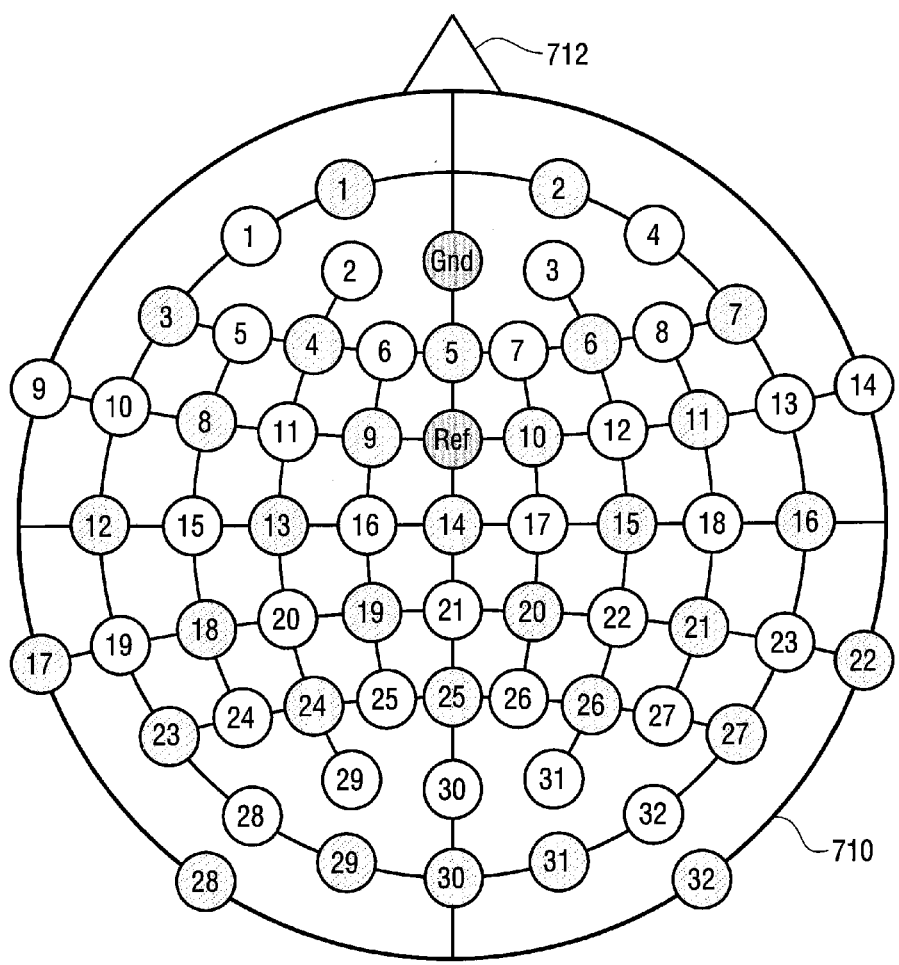
FIG. 13 is a schematic representation of EEG channels locations.

EEG signals were recorded by a standard 64-channel EEG device 710. Location of channels is shown schematically in FIG. 13. As shown in FIG. 13, the subject's nose 712 orients the cap 710 to place half the sensors on each side of the subject's head. The first 32 channels are shown by grey circles, while the second 32 channels, from channel 33 to channel 64, are shown by white circles, and their numbering is obtained by adding of 32 to the numbers in white circles.

First, we computed the correlation coefficients defined by Eq. (5b) but at the same time intervals, i.e. at n=m, $P_{eeg}(n, n, \alpha, \beta)$, where n=1÷15 numerates the time intervals, while $\alpha$=1÷64 and $\beta$=1÷64, numerate the EEG channels according to schematics presented in FIG. 5.

Figure 14:
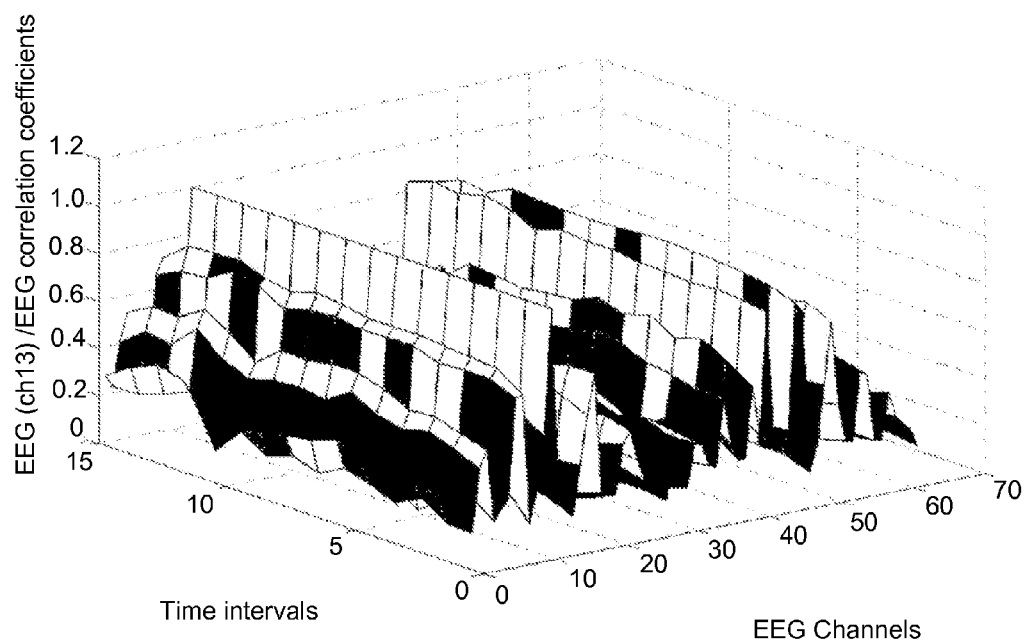
FIG. 14 is a graphic representation showing the time dependence of Pearson correlation coefficients for a healthy control between channel 13 and all other channels.

FIG. 14 represents the correlation coefficients for channel 13 and all other channels, $P_{eeg}(n, \alpha=13, \beta)$, for all time intervals for a control healthy subject. It is easily seen that the time dependence is quite weak for all correlators. And analogous time behavior is observed for both healthy subjects and PD patients. That allows us to average the correlation coefficients over time intervals $$P_{mean}(\alpha, \beta) = \frac{1}{M} \sum_{n=1}^{M} P(n, \alpha, \beta) \quad (6)$$

where M=15 is the number of time intervals.

Figure 15:
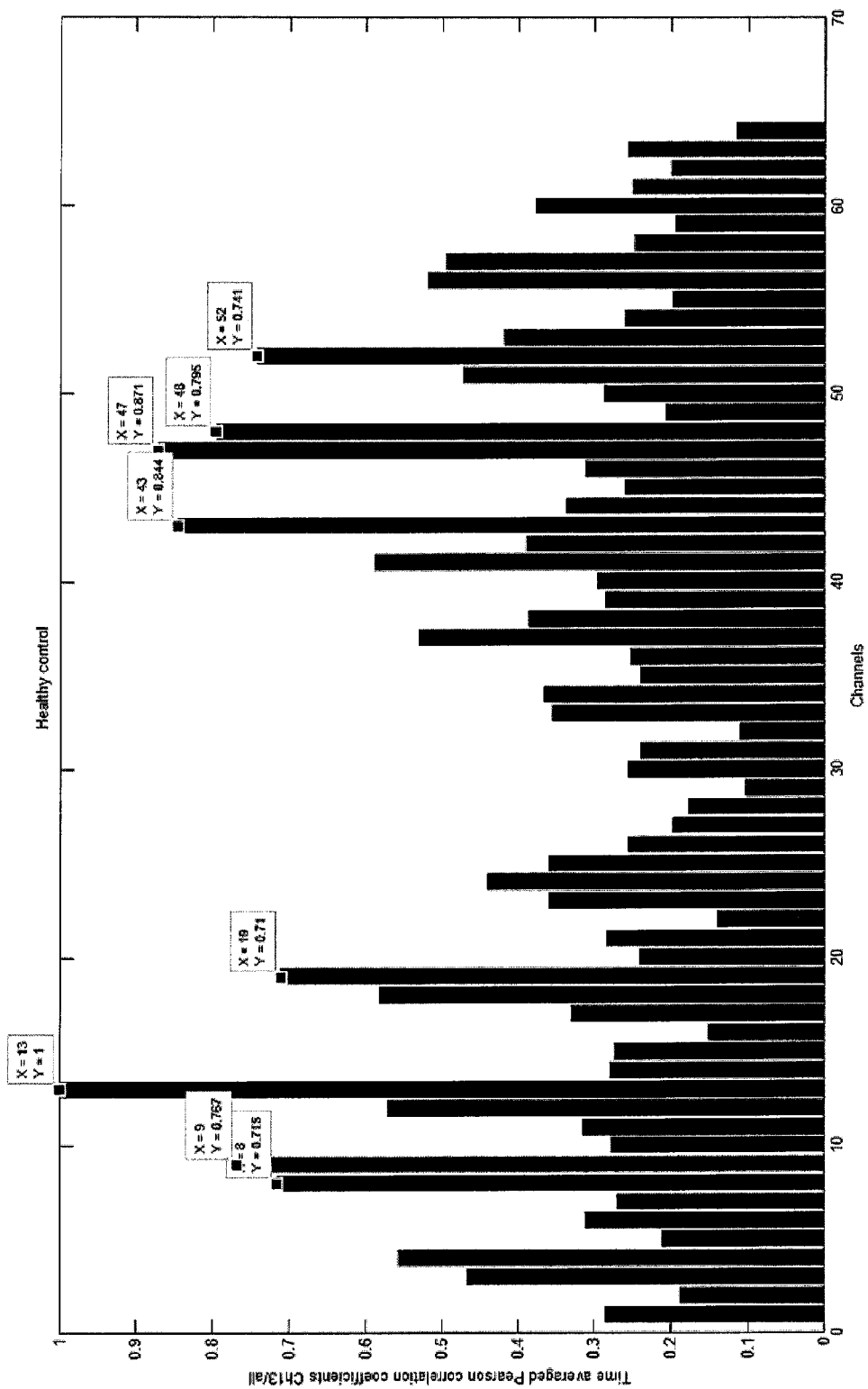
FIG. 15 is a graphic representation showing Pearson correlation coefficients Pmean of channel 13 (C3) with all channels during handwriting (healthy control)
Figure 16:
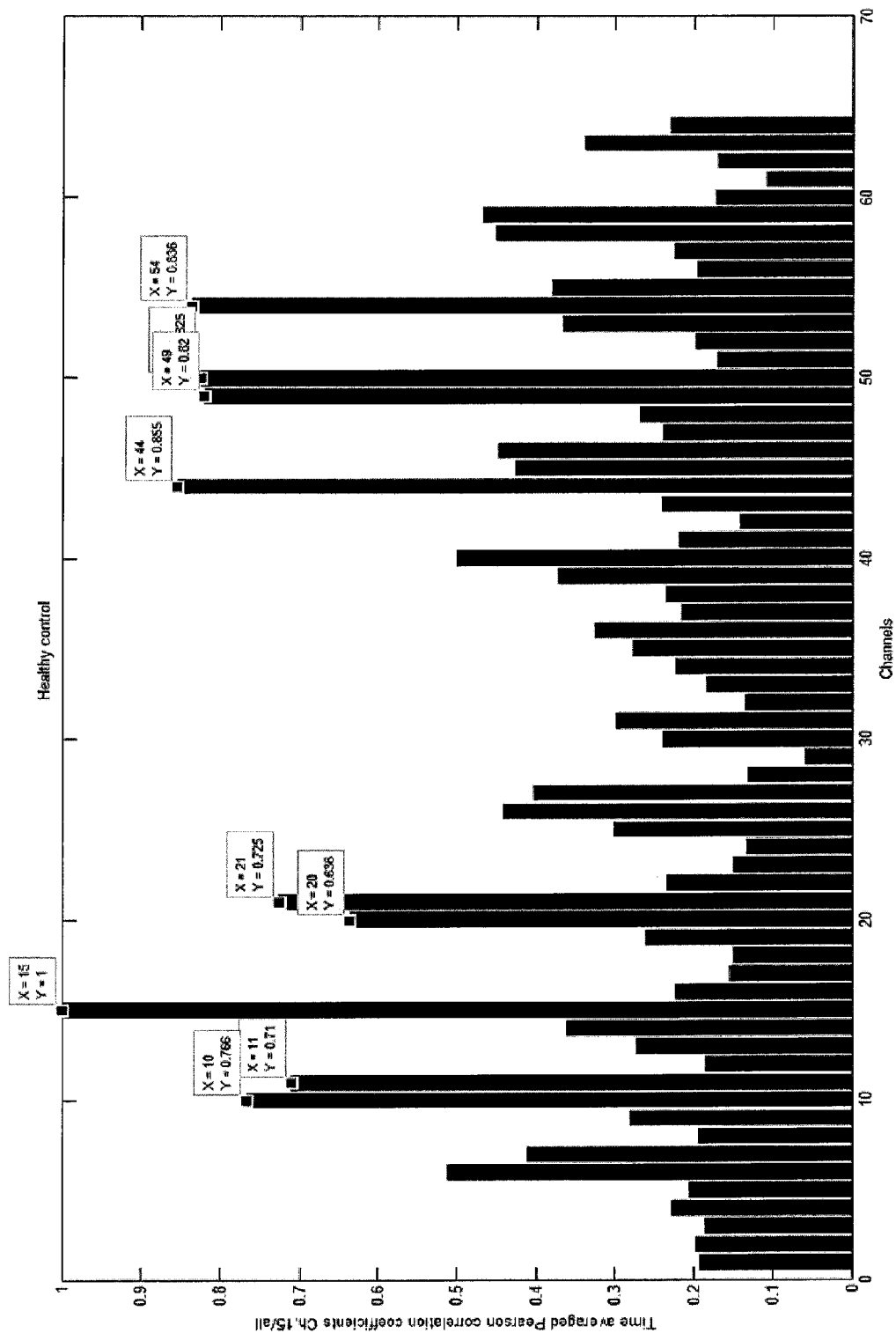
FIG. 16 is a graphic representation showing Pearson correlation coefficients Pmean of channel 15 (C4) with all channels during handwriting (healthy control).
Figure 17:
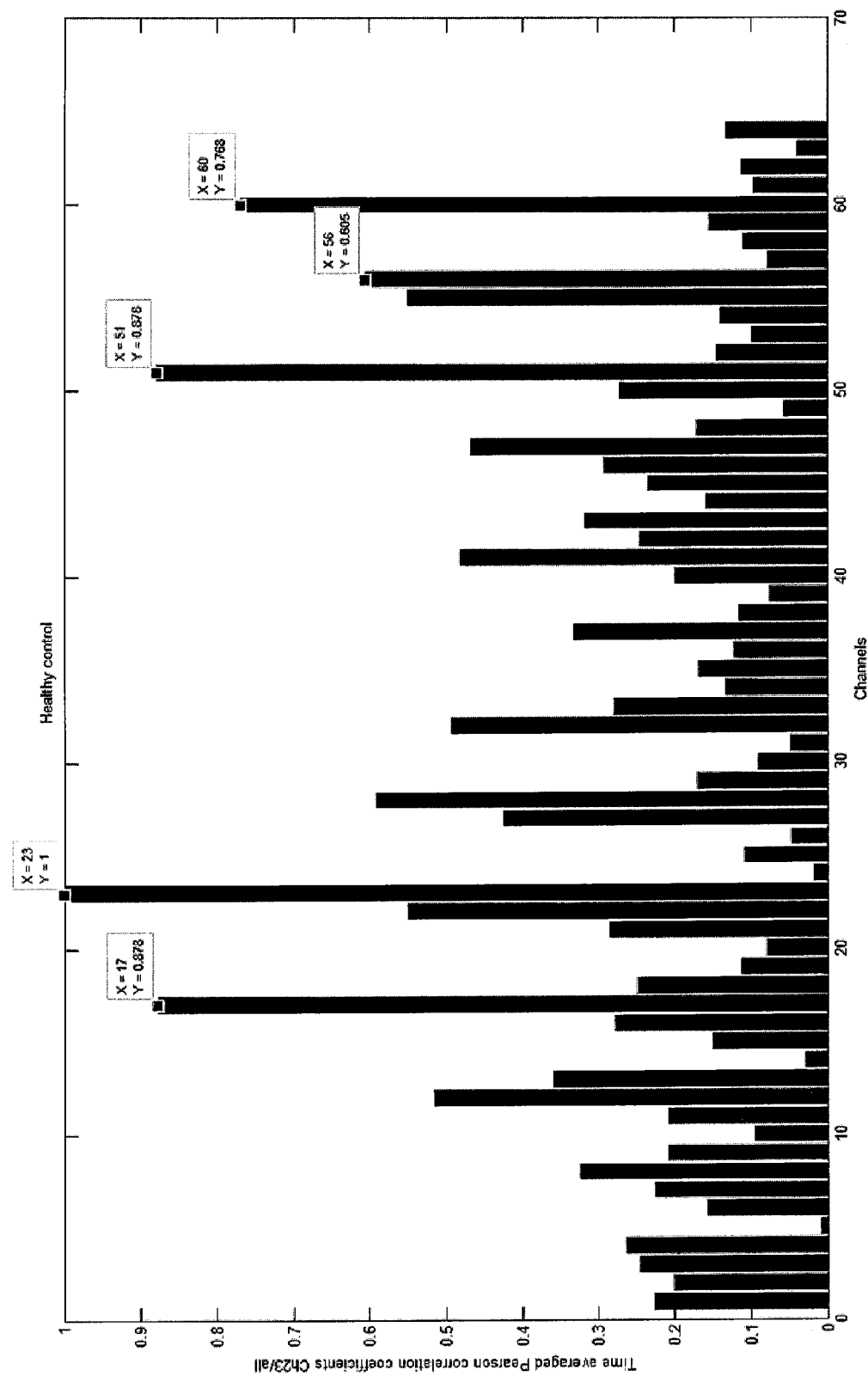
FIG. 17 is a graphic representation showing Pearson correlation coefficients Pmean of channel 23 (P7) with all channels during handwriting (healthy control).
Figure 18:
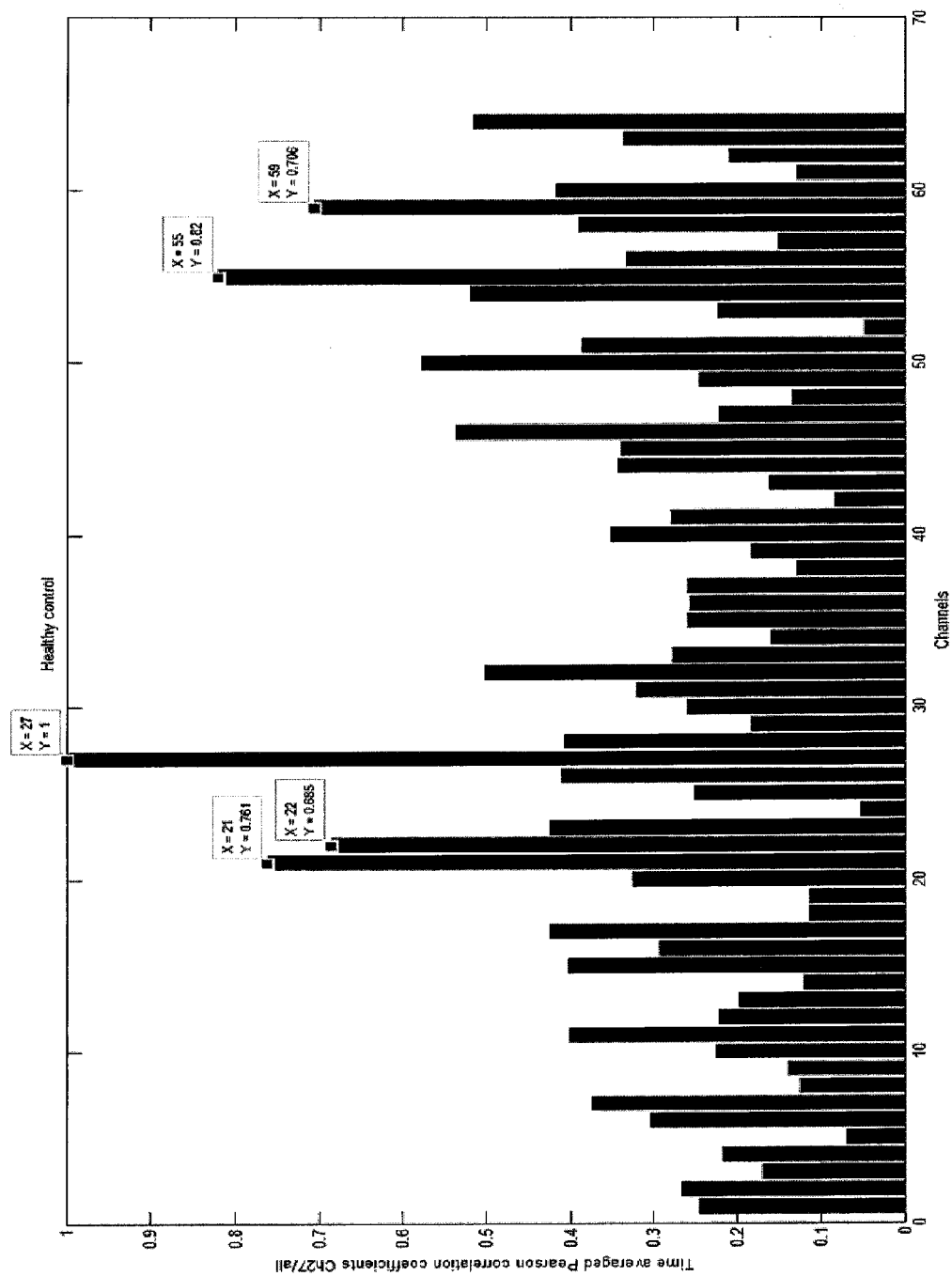
FIG. 18 is a graphic representation showing Pearson correlation coefficients Pmean of channel 27 (P8) with all channels during handwriting (healthy control).

FIGS. 15-18 show time-averaged Pearson correlation coefficients $P_{mean}$ for channels 13(C3) 722a, 15(C4) 751a, 23(P7) 724a, and 27(P8) 723a, respectively, with all other channels, computed for a healthy control subject. The channel numbers are vendor specific. In parenthesis are the names of channels according to the international naming convention. The channels are defined by the boundary surrounding the indicated sensors. FIG. 15 shows the Pearson correlation coefficients $P_{mean}$ of channel 13 (C3) with all channels during handwriting (healthy control). FIG. 16 shows Pearson correlation coefficients $P_{mean}$ of channel 15 (C4) with all channels during handwriting (healthy control). FIG. 17 shows Pearson correlation coefficients $P_{mean}$ of channel 23 (P7) with all channels during handwriting (healthy control). FIG. 18 shows Pearson correlation coefficients $P_{mean}$ of channel 27 (P8) with all channels during handwriting (healthy control).

Figure 19:
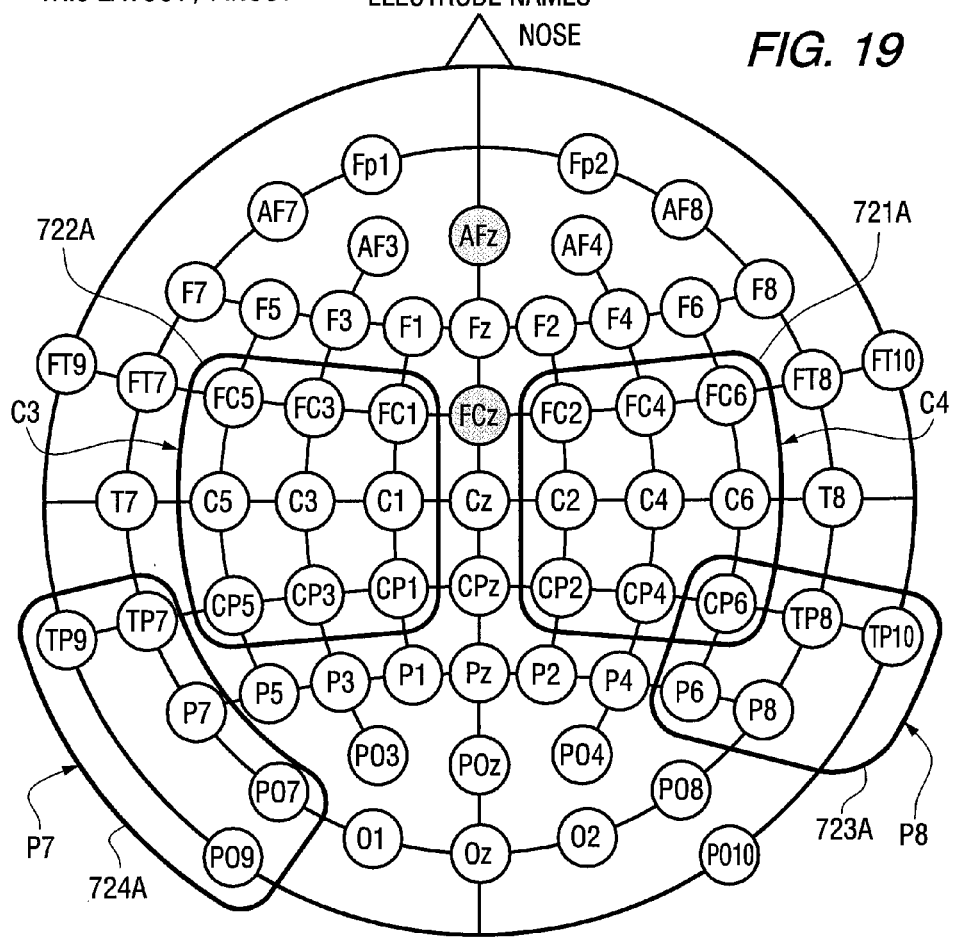
FIG. 19 is a graphic representation showing healthy control cortex activity regions using the International naming convention.
Figure 20:
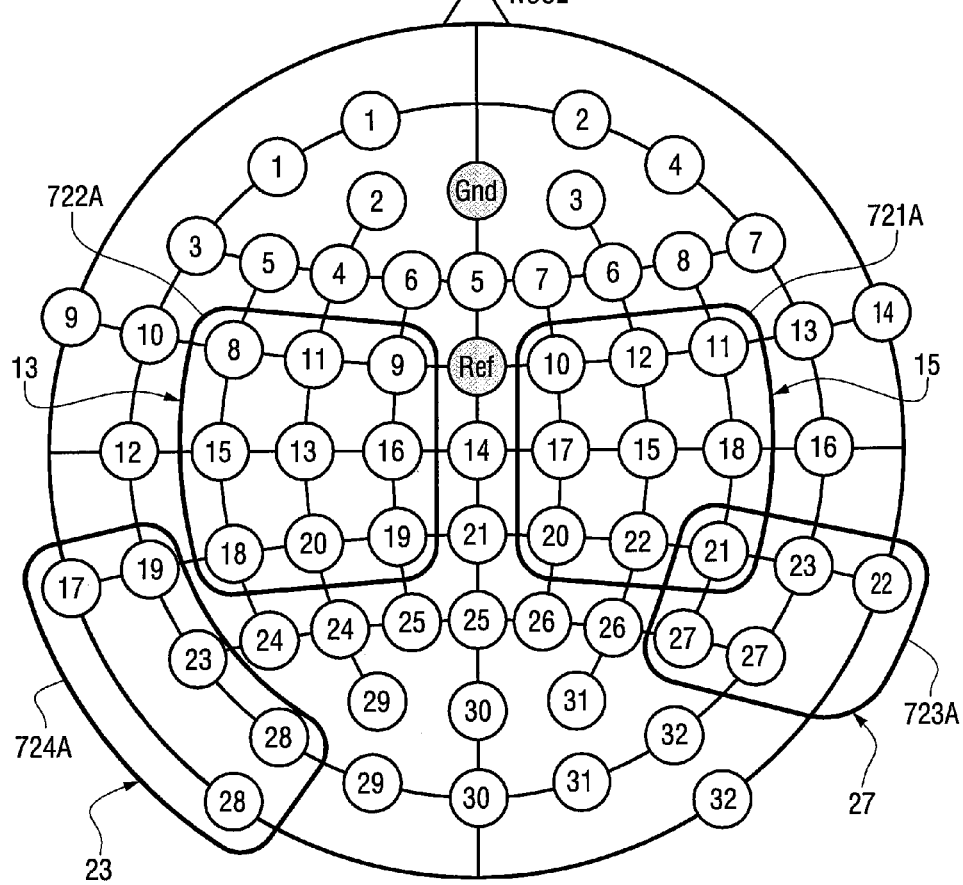
FIG. 20 is a graphic representation showing healthy control cortex activity regions using a vendor specific naming

An EEG activity of healthy control subjects during handwriting is localized in, at least, four relatively small regions around the channels 13(C3) and 23(P7) on the left hemisphere and symmetrically around the channels 15(C4) and 27(P8) on the right hemisphere. Correlation coefficients are large for channels inside regions and significantly fall down for channels, which belong to different regions, as shown in FIG. 19, 20.

Figure 21:
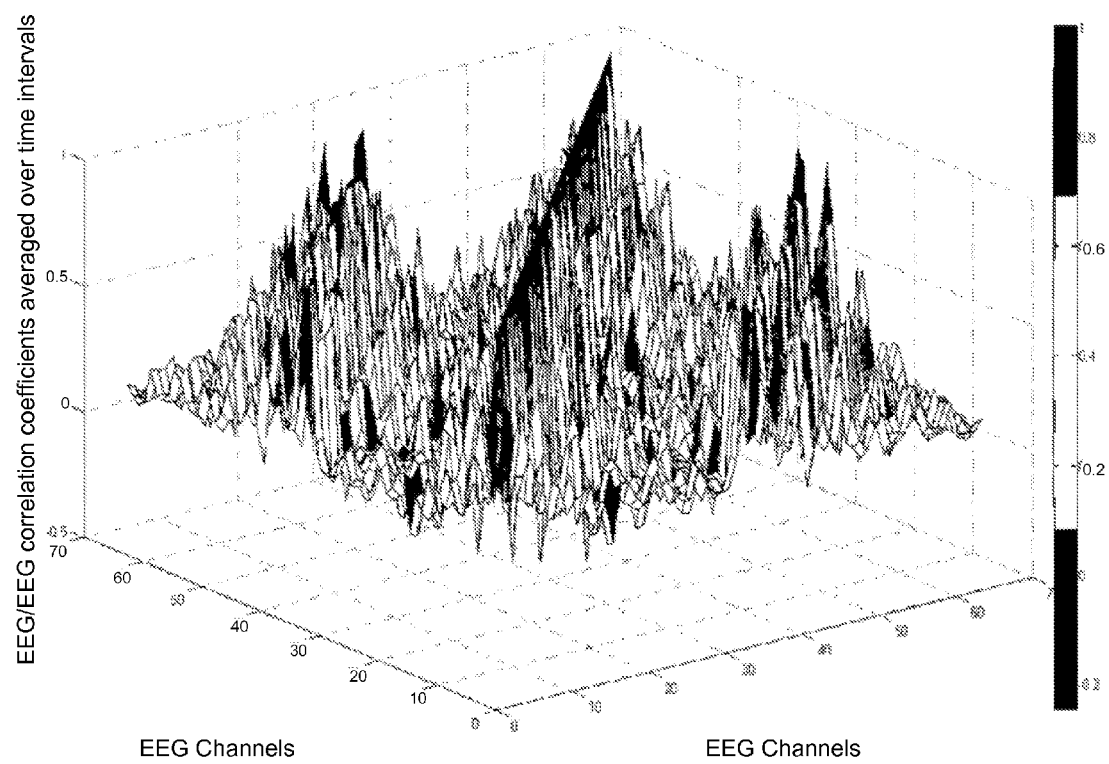
FIG. 21 is a graphic representation showing correlation coefficients $P_{mean}$ computed for control healthy subject.
Figure 22:
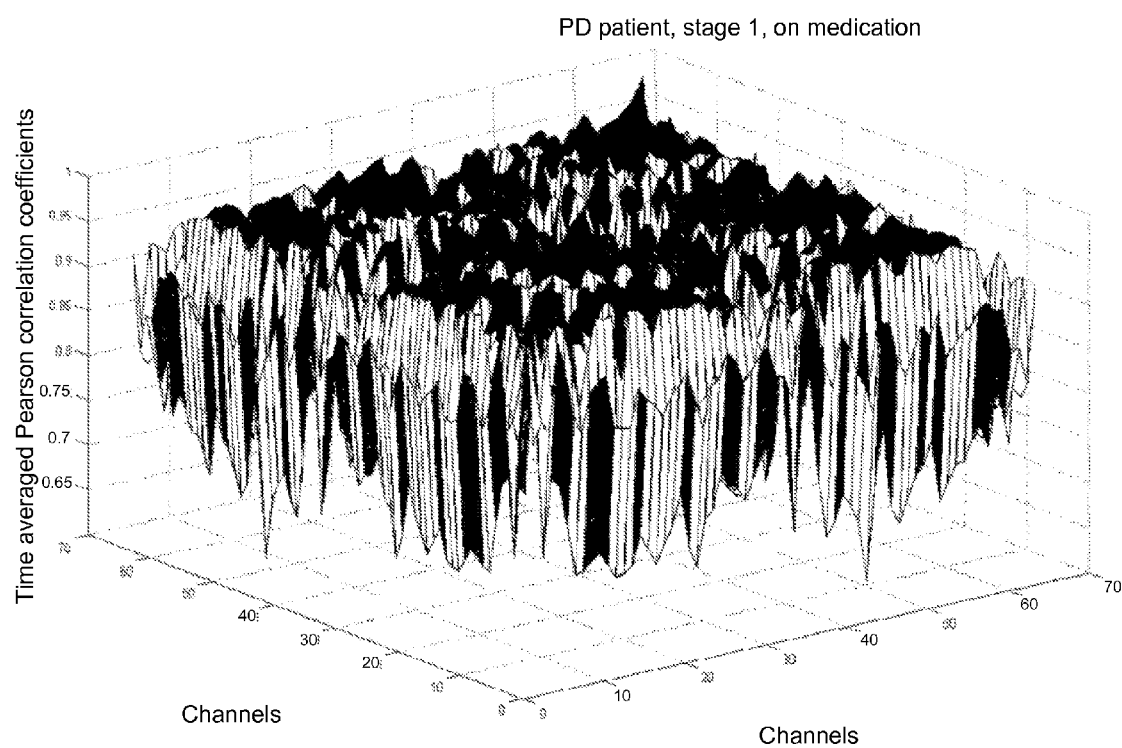
FIG. 22 is a graphic representation showing a PD patient, stage I, on medication with high correlations between all cortex channels.
Figure 23:
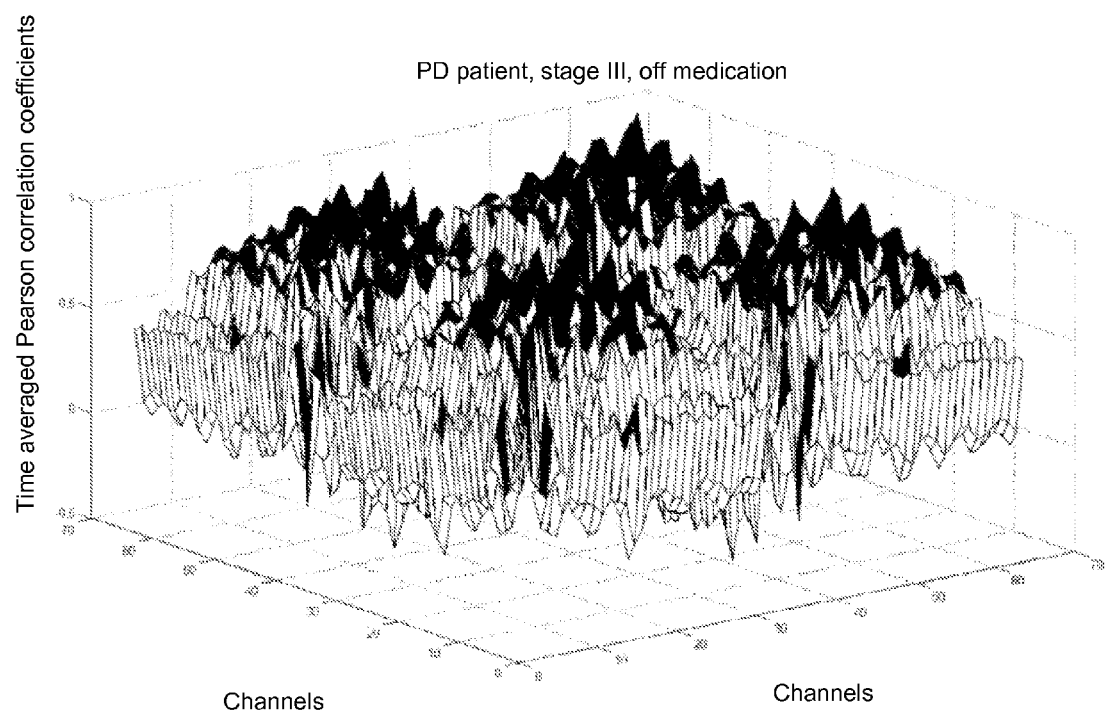
FIG. 23 is a graphic representation showing a PD patient, stage III, off medication with high correlations between all cortex channels.

FIGS. 21-23 represent the correlation coefficients $P_{mean}$ computed for healthy control subject (FIG. 21) and PD patients (FIGS. 22, 23) at stage I and III, respectively, of disease. As one can see from FIG. 21, the healthy control does not have a lot of highly correlated channels during handwriting, because most of the correlation coefficients are relatively low. However, FIG. 22 shows results of a patient in Stage I PD and FIG. 23 shows results for a patient in Stage III PD. Both figures show relatively highly and broad, non-localized correlations. Thus, an EEG activity of PD patients is delocalized and extended to practically whole cortex, because correlation coefficients between almost all channels on both hemispheres are large and shown in red, as easily seen in FIGS. 22 and 23.

Growth of a Characteristic Correlation Time of EEG Signals

We also computed the correlation functions in equation (5b), $P_{eeg}$ (n, m, α, β), for EEG signals depending on two sets of time intervals, n=1÷15 and m=1÷15. This allows one for estimating a characteristic correlation time for a single channel and for two different channels.

Figure 24:
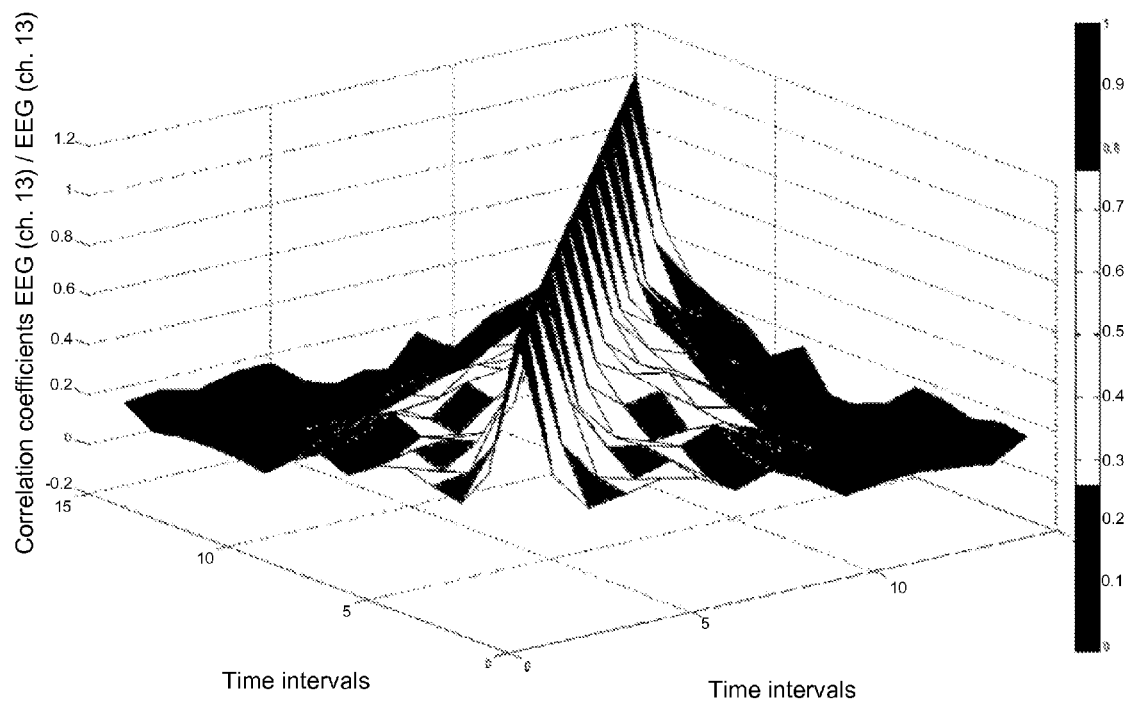
FIG. 24 is a graphic representation showing correlation coefficients of EEG signal (channel 13) of healthy control subject as a function of two time intervals.

FIG. 24 represents the correlation coefficient for a single channel 13, $P_{eeg}$ (n, m, α=13, β=13), of a healthy control subject as a function of two time intervals. The correlation coefficient is naturally equal to 1 along the diagonal n=m, and falls down when the time intervals are different. It decreases from 1 to about 0.3 already for n=m±1. That means that a characteristic correlation time can be estimated as 100 ms or shorter.

More precise measurements require more accurate synchronization of bio-signal trials. That hardly can be done, because of neuronal variability during handwriting [2]. For example, even time of pen motion is varied from trial to trial in quite wide limits of the order of 50-100 ms. An analogous time behavior with the characteristic correlation time of the order of 100 ms (or shorter) we also observe for correlation coefficients computed for two different channels provided they belong to one of above-discussed activity regions.

Figure 25:
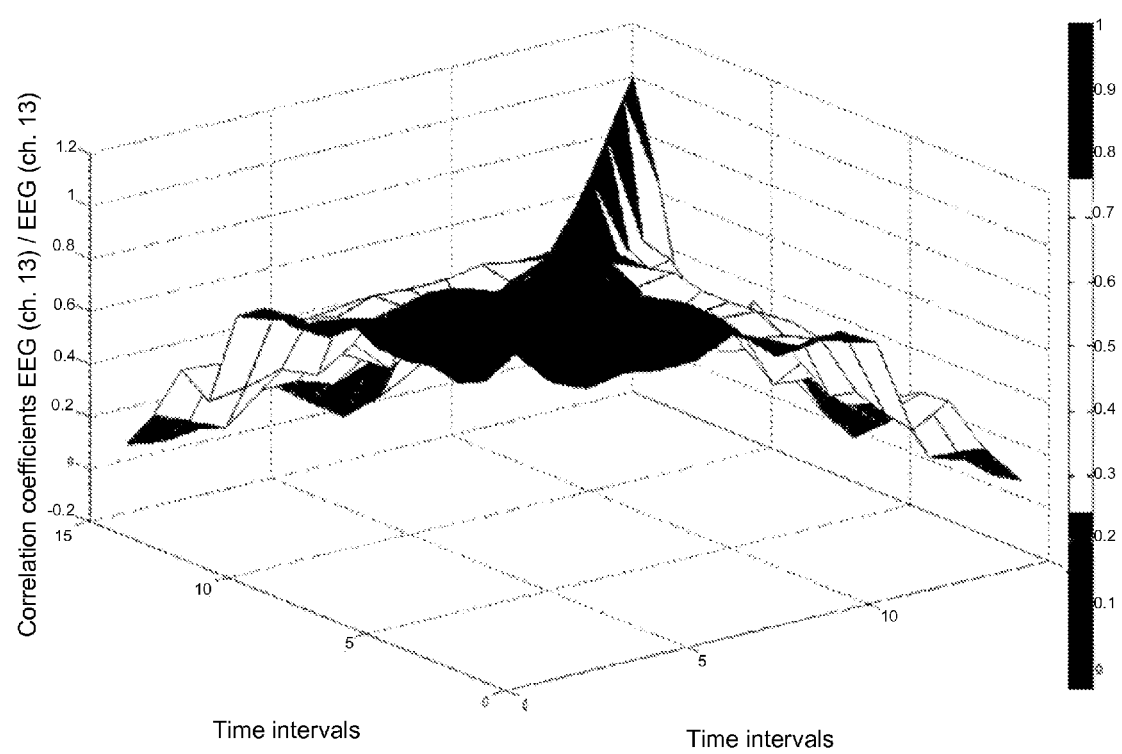
FIG. 25 is a graphic representation showing correlation coefficient of EEG signal (channel 13) of PD patient as a function of two time intervals.

However, for PD patients we observed a significant increase of the characteristic correlation time, as can be easily seen from FIG. 25. An EEG activity correlates even for large difference between time intervals, |n−m|, especially for time intervals before the moment of time when a pen touches a paper (intervals 1÷5) and during handwriting itself (intervals 6÷10).

REFERENCES

1. Linderman, M., Lebedev, M. A and Erlichman, J. S. Recognition of handwriting from electromyography, *PLoS One* 4 (8) (2009).
2. Rupasov, V. I., Lebedev, M. A., Erlichman, J. S., and Linderman, M. Neuronal variability during handwriting: Lognormal distribution, submitted for publication.
3. Bendat, J. S. and Piersol, A. G. Measurements and analysis of random data (John Wiley & Sons, New York, USA, 1968).

Alternate Configurations

A machine-readable medium includes any mechanism that provides (i.e., stores and/or transmits) information in a form readable by a machine (e.g., a computer). For example, a machine-readable medium includes, but is not limited to, read only memory (ROM); random access memory (RAM); magnetic disk storage media; optical storage medial; flash memory devices; electrical, optical, acoustical or other form of propagated signals (e.g., carrier waves, infrared signals, digital signals, etc.); storage media; radio channels; and wireless channels and various other mediums capable of storing, containing, or carrying instructions and/or data.

It is possible to provide a variety of alternative configurations for implementing the technique. By way of example, the glove, a sleeve, or some other article of apparel can be adapted to fit on a part of the body, other than the hand, which is capable of receiving nerve impulses for fine motor control. Examples include the feet and face. In that manner, the sensed EMG signals can be used for biometric assessment. It is further possible to use such EMG signals for robotic manipulation or for sending signals for computer processing. In that manner, fine manipulations may be possible without the use of the hands.

The previous description of some embodiments is provided to enable any person skilled in the art to make or use the present technique. Various modifications to these embodiments will be readily apparent to those skilled in the art, and the generic principles defined herein may be applied to other embodiments without departing from the spirit or scope of the present disclosure. For example, one or more elements can be rearranged and/or combined, or additional elements may be added. Further, one or more of the embodiments can be implemented by hardware, software, firmware, middleware, microcode, or any combination thereof. Thus, the present disclosure is not intended to be limited to the embodiments shown herein but is to be accorded the widest scope consistent with the principles and novel features disclosed herein.

Having described the technique in detail and by reference to the embodiments thereof, it will be apparent that modifications and variations are possible, including the addition of elements or the rearrangement or combination or one or more elements, without departing from the scope of the disclosure which is defined in the appended claims.

The invention claimed is:

1. A method of detecting a disorder of the central nervous system, comprising:
   collecting EMG signals corresponding to a defined handwriting activity over a plurality of trials;
   squaring one or more amplitudes of the collected EMG signals to obtain one or more signal intensities;
   subdividing the obtained signal intensities into a plurality of time intervals;

calculating an energy value for each of the plurality of time intervals;

normalizing the energy values for each of the plurality of time intervals;

computing a log-normal trial-to-trial distribution of the normalized energy values in each time interval;

computing correlation functions between two time intervals of the plurality of time intervals;

analyzing the correlation functions to distinguish healthy controls from patients with neurological disorders.

2. A method of detecting a disorder of the central nervous system, comprising:

collecting EEG signals corresponding to a defined handwriting activity over a plurality of trials;

squaring one or more amplitudes of the collected EEG signals to obtain one or more signal intensities;

subdividing the obtained signal intensities into a plurality of time intervals;

calculating an energy value for each of the plurality of time intervals;

normalizing the energy values for each of the plurality of time intervals;

computing a log-normal trial-to-trial distribution of the normalized energy values in each time interval;

computing correlation functions between two time intervals of the plurality of time intervals;

analyzing the correlation functions to distinguish healthy controls from patients with neurological disorders.

3. A method of detecting a disorder of the central nervous system, comprising:

simultaneously collecting EMG signals and EEG signals corresponding to a defined handwriting activity over a plurality of trials;

squaring one or more amplitudes of the collected EMG signals and the collected EEG signals to obtain one or more signal intensities;

subdividing the obtained signal intensities into a plurality of time intervals;

calculating an energy value for each of the plurality of time intervals;

normalizing the energy values for each of the plurality of time intervals;

computing a log-normal trial-to-trial distribution of the normalized energy values in each time interval;

computing correlation functions between two time intervals of the plurality of time intervals;

analyzing the correlation functions to distinguish healthy controls from patients with neurological disorders.

* * * * *